(12) United States Patent
Robinson et al.

(10) Patent No.: US 10,719,691 B2
(45) Date of Patent: Jul. 21, 2020

(54) CULTURE IMAGING SYSTEM

(71) Applicant: Purdue Research Foundation, West Lafayette, IN (US)

(72) Inventors: Joseph Paul Robinson, West Lafayette, IN (US); Bartlomiej P. Rajwa, West Lafayette, IN (US); Kathryn E. Ragheb, West Lafayette, IN (US); Cheryl M. Holdman, Brookston, IN (US); Valery P. Patsekin, West Lafayette, IN (US); Euiwon Bae, West Lafayette, IN (US); Jennifer Sturgis, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 281 days.

(21) Appl. No.: 15/565,404

(22) PCT Filed: Apr. 21, 2016

(86) PCT No.: PCT/US2016/028712
§ 371 (c)(1),
(2) Date: Oct. 9, 2017

(87) PCT Pub. No.: WO2016/172387
PCT Pub. Date: Oct. 27, 2016

(65) Prior Publication Data
US 2018/0129864 A1    May 10, 2018

Related U.S. Application Data

(60) Provisional application No. 62/150,716, filed on Apr. 21, 2015, provisional application No. 62/150,754, filed on Apr. 21, 2015.

(51) Int. Cl.
*G06K 9/00* (2006.01)
*G06T 7/00* (2017.01)
(Continued)

(52) U.S. Cl.
CPC ........ *G06K 9/00147* (2013.01); *C12M 41/36* (2013.01); *G02B 21/365* (2013.01);
(Continued)

(58) Field of Classification Search
None
See application file for complete search history.

(56) References Cited

U.S. PATENT DOCUMENTS 6,979,828 B2 * 12/2005 Tokuda ............... C12Q 1/04
250/461.2
7,465,560 B2 * 12/2008 Hirleman, Jr. ......... G01N 21/21
435/34
(Continued)

FOREIGN PATENT DOCUMENTS

EP    1502649    2/2005

OTHER PUBLICATIONS

Tang, et al., "Light Scattering Sensor for Direct Identification of Colonies of *Escherichia coli* Serogroups 026, 045, 3103, 0111, 0121, 0145 and 0157", PLOS One, vol. 9, No. 8, Aug. 19, 2014, p. e105272 (Year: 2014).*
(Continued)

*Primary Examiner* — Anand P Bhatnagar
(74) *Attorney, Agent, or Firm* — Purdue Research Foundation

(57) ABSTRACT

A system for the characterization of a colony of microorganisms includes a coherent light source configured to provide coherent light of one or more wavelengths along a common optical path. A holder is configured to operationally arrange a substrate so that the colony of microorganisms on a surface of the substrate is positioned to receive the coherent light. Scattered light is generated from the colony of microorganisms receiving coherent light. A first image capture device is configured to receive the scattered light
(Continued)

and generate a scatter image from the microorganism colony irradiated by the coherent light. The system also includes a magnifying lens configured to magnify the colony of microorganisms. A second image capture device is configured to capture a light image of the colony of microorganisms magnified by the magnifying lens. Methods of assigning organisms to categories with like organisms without necessarily identifying the organisms are also described.

5 Claims, 22 Drawing Sheets

(51) Int. Cl.
*C12M 1/34* (2006.01)
*G02B 21/36* (2006.01)

(52) U.S. Cl.
CPC ....... *G06K 9/0014* (2013.01); *G06K 9/00134* (2013.01); *G06T 7/0012* (2013.01); *G06T 2207/10056* (2013.01); *G06T 2207/30024* (2013.01)

(56) References Cited

U.S. PATENT DOCUMENTS

| 8,787,633 | B2* | 7/2014 | Robinson | G06K 9/0014 382/100 |
| 9,250,238 | B2* | 2/2016 | Low | G01N 33/54353 |
| 9,482,659 | B2* | 11/2016 | Loewke | G01N 35/00584 |
| 2003/0155528 | A1* | 8/2003 | Tokuda | C12Q 1/04 250/461.2 |
| 2010/0182419 | A1* | 7/2010 | Jiang | B01L 9/523 348/79 |
| 2010/0315628 | A1* | 12/2010 | Mertsching | G01N 15/1463 356/301 |
| 2013/0129181 | A1* | 5/2013 | Glensbjerg | G01N 15/1475 382/133 |
| 2013/0194410 | A1* | 8/2013 | Topman | G06K 9/0014 348/79 |
| 2014/0160236 | A1* | 6/2014 | Ozcan | G02B 21/367 348/40 |
| 2015/0324969 | A1* | 11/2015 | DenBrok | G06K 9/00147 382/110 |
| 2017/0219485 | A1* | 8/2017 | Bae | G01N 21/255 |
| 2018/0079999 | A1* | 3/2018 | Blanchard | C12M 23/16 |

OTHER PUBLICATIONS

PCT Invitation to Pay Additional Fees dated Jul. 13, 2014 for PCT application No. PCT/US2016/028712, 10 pages.
PCT Search Report and Written Opinion dated Sep. 5, 2016 for PCT Application No. PCT/US16/28712, 20 pages.
Tang, et al., "Light Scattering Sensor for Direct Identification of Colonies of *Escherichia coli* Serogroups O26, O45, O103, O111, O121, O145 and O157", PLOS One, vol. 9, No. 8, Aug. 19, 2014, p. e105272.

* cited by examiner

13:05 hrs    15:15 hrs    17:05 hrs

19:02 hrs    21:02 hrs    23:03 hrs

25:07 hrs    27:08 hrs    29:10 hrs

30:28 hrs    32:26 hrs

CULTURE IMAGING SYSTEM

CROSS-REFERENCE TO RELATED APPLICATIONS

This application is a 35 USC § 371 filing of International Application PCT/US2016/028712 filed Apr. 21, 2016, and entitled "Culture Imaging System," which claims priority to, and the benefit of, U.S. Provisional Patent Application Ser. No. 62/150,716, filed Apr. 21, 2015, and entitled "Culture Imaging System" and U.S. Provisional Patent Application Ser. No. 62/150,754, filed Apr. 21, 2015, and entitled "Culture Identification," the entirely of which are incorporated herein by reference.

STATEMENT OF FEDERALLY SPONSORED RESEARCH OR DEVELOPMENT

This invention was made with Government support under Contract Nos. AI085531 and AI089511 awarded by the National Institutes of Health and under Contract No. 59-1935-2-279 awarded by the United States Department of Agriculture. The government has certain rights in the invention.

TECHNICAL FIELD

The present application relates to characterizing, classifying, or identifying microscopic structures. Various aspects relate to such structures including, e.g., colonies of microorganisms, clusters of cells, or organelles.

BACKGROUND

Rapid identification and classification of microbial organism is a useful task in various areas, such as biosurveillance, biosecurity, clinical studies, and food safety. There is, for example, a need for methods for monitoring and detecting pathogenic microorganism such as *Escherichia coli, Listeria, Salmonella*, and *Staphylococcus*.

BRIEF DESCRIPTION

A system for the characterization of a colony of microorganisms includes a coherent light source configured to provide coherent light of one or more wavelengths along a common optical path. A holder configured to operationally arrange a substrate so that the colony of microorganisms on a surface of the substrate is positioned to receive the coherent light. Scattered light is generated from the colony of microorganisms receiving the coherent light. A first image capture device is configured to receive the scattered light and generate a scatter image from the microorganism colony irradiated by the coherent light. The system also includes a magnifying lens configured to magnify the colony of microorganisms. A second image capture device is configured to capture a light image of the colony of microorganisms magnified by the magnifying lens. Methods of assigning organisms to categories with like organisms without necessarily identifying the organisms are also described.

This brief description is intended only to provide a brief overview of subject matter disclosed herein according to one or more illustrative embodiments, and does not serve as a guide to interpreting the claims or to define or limit scope, which is defined only by the appended claims. This brief description is provided to introduce an illustrative selection of concepts in a simplified form that are further described below in the Detailed Description. This brief description is not intended to identify key features or essential features of the claimed subject matter, nor is it intended to be used as an aid in determining the scope of the claimed subject matter. The claimed subject matter is not limited to implementations that solve any or all needs or disadvantages noted in the Background.

BRIEF DESCRIPTION OF THE DRAWINGS

Various objects, features, and advantages of the present invention will become more apparent when taken in conjunction with the following description and drawings wherein identical reference numerals have been used, where possible, to designate identical features that are common to the figures, and wherein:

In FIG. 6, a plate holder can be used to retain a plate, or a plate can be used without a holder;

FIG. 7 shows a graphical representation of a photograph of a test system configured to hold multiple plates according to various aspects;

Figure 1A:
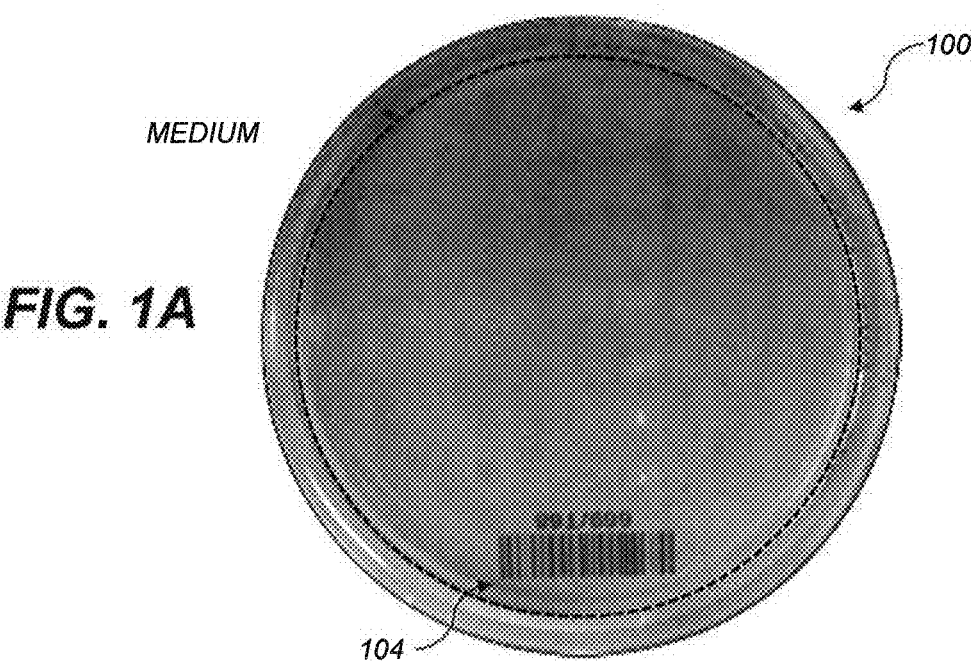
FIG. 1A shows a culture plate holding an agar growth medium and having a 1-D barcode.

The attached drawings are for purposes of illustration and are not necessarily to scale.

DETAILED DESCRIPTION

Various aspects relate to using multiple modalities to image microbial colonies on a substrate. Various aspects relate to grouping microbial colonies with similar traits into shared clusters. Various aspects relate to time-based analysis of microbial colonies on a substrate. Various aspects relate to tracking a particular microbial colony on a substrate when an orientation of the substrate is changed.

This detailed description is divided into subsections solely for clarity of exposition. No limitation is implied or should be inferred by any subsection header or division. Some examples may, but are not required to, include combining components or techniques from multiple subsections.
Illustrative Imaging Systems and Techniques Laser scattering phenomena from bacterial colonies has provided a possible label-free discrimination methodology, named Bacteria Rapid Detection using Optical scattering Technology (BARDOT). As used herein, the term BARDOT refers to systems or techniques according to various examples described herein. The term "BARDOT" does not imply or require any particular manufacturer or trade name of equipment, or any particular provider or trade name of services. BARDOT has been shown to permit classifying bacterial colonies as to the subspecies of bacteria in the colony, e.g., at the serovar level. Compared to other detection methods, label-free optical diagnostics delivers fast and accurate results, and provides cost-effective and non-destructive evaluation of the samples, allowing for secondary confirmation with further verification. A BARDOT system may include a coherent light source (e.g., a laser), producing a beam of coherent light having a diameter (e.g., full-width at half-maximum or $1/e^2$) of ~1 mm, that illuminates or irradiates a bacterial colony on a substrate. The substrate may be a Petri dish, plate, glass slide, or the like and the substrate may also be agar or other media upon which the colonies may grow. Laser energy or power levels, or total energy, can be low enough to cause no or substantially no damage to the colony or bacteria therein. A resulting diffraction pattern, or "scatter pattern," fingerprints the colony. A colony of what may be a plurality of colonies may be disposed to be illuminated by an optical radiation source, where the optical wavelength regime may be one or more wavelengths in the range of about 300 nm to about 800 nm. The optical radiation may be generated by a laser source, which may be a semiconductor laser, a gas laser, or the like. Laser light sources are known to have a coherent radiation characteristic. The coherence of each type of laser may be different, and may vary with such parameters as the laser current. For this reason, it should be understood that the term "coherent" light source encompasses a substantially coherent light source.

A colony can be measured in ~1 sec per colony. This permits identifying bacteria without using reagents or other chemicals. The embodiments and methods described refer to bacterial colonies, however, the present invention may also be used for identification and characterization of other microorganisms and is not limited to only the bacteria or the bacterial examples described below. The diffraction pattern is based, e.g., on at least some of the nature of the colony (which is based on the organism), the colony size (which is correlated with organism type), the growth medium (e.g., agar), chemicals (e.g., polysaccharides) that bacteria in the colony produce or contain, position of bacteria in the colony, whether the bacteria produce pigments, and how many of the bacteria are alive or dead. The diffraction pattern is generally consistent for a particular organism in a particular medium. Bacterial colonies have two major regions: edge regions that are generally less dense, have greater water content, and wherein division of cells occurs, and the center part. The pattern information can provide some understanding on how the bacteria are spreading at the edge and how cells are accumulating at the center part.

In an aspect, a plurality of images of a specific colony type associated with a specific genotype may be analyzed to determine the identifying characteristics or features extracted from the image by numerical analysis methods, to train a characterizing algorithm to identify the genotype of a colony sample of an unknown organism.

Colonies can be identified from diffraction patterns using machine-learning techniques that learn to differentiate various diffraction patterns. For example, a support vector machine (SVM) classifier can be used with features based on orthogonal moments of shape. Colonies are generally stationary in a growth medium. In some examples, the diffraction pattern is independent of the orientation of the colony or is independent of the orientation of the plate. In some examples, the machine-learning system can identify diffraction patterns regardless of the orientations of the colony or the plate. The diffraction pattern can permit distinguishing bacterial colonies from air bubbles.

The laser can be passed directly through the colony and an image sensor positioned at the focal plane of the diffraction pattern. Lenses or other optics, e.g., infinity-corrected microscope optics, can alternatively be used to focus the laser light or the diffraction pattern.

Recently, there has been developed a label-free colony based bacterial classification system which utilizes the single 635 nm wavelength for interrogation. Various examples of the system can be used for classifying genus and species levels and some cases down to serovar levels. Bacterial colonies can be modeled as a biological spatial light modulator which changes the amplitude and phase of the outgoing wave and the characteristics of the scatter patterns to the morphological trait of the individual colonies were closely investigated. Various colonies have profiles such as convex shapes with different radii of curvature and a Gaussian profile. For example, a profile of a *Staphylococcus Aureus* (*S. aureus*) colony can closely match a Gaussian curve, which is similar to a bell curve with a tailing edge with smaller aspect ratio (colony height to diameter ratio). In a tested example, a measured colony generated a concentric circular diffraction pattern.

One method of characterizing and differentiating bacterial colonies using forward light scattering patterns may be accomplished by assigning certain values to individual unique features in the scattering patterns. In general, the scattering pattern of a bacterial colony may include some radial symmetry, and may be composed of diffraction ring(s). Generally, a spot at the center of the scattering pattern may be included, with size and sharpness varying from strain to strain. Usually at least one ring may be present, and there may be 2, 3, 4 or more rings. The size, thickness, sharpness, and intensity of the ring(s) may also vary from strain to strain. For some strains, there may be diffusion around the innermost ring, and for other strains radial spikes may be present outside of the innermost ring. The integrated intensity of the entire scattering pattern also may vary from stain to strain.

In one embodiment, scattering patterns from samples may be scored according to the features and the samples may be characterized according to the scores. Feature detection and scoring may be automatically performed by machine vision and image analysis techniques operating on images captured by various image capture devices. The specific characteristics illustrate one set of scattering pattern features that will allow automated detection and classification of bacteria using forward scattering. One of skill in the art will recognize that additional sets of scattering pattern features and additional approaches of scoring or processing said scattering pattern features may be used.

Figure 1B:
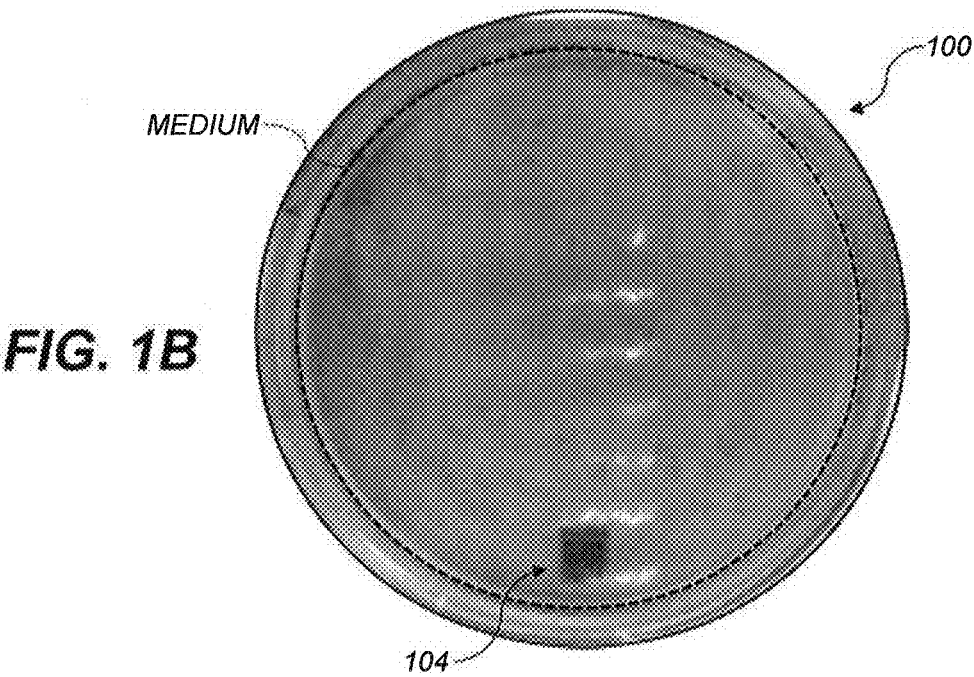
FIG. 1B shows a culture plate holding an agar growth medium and having a QR code (an example 2-D barcode)

FIGS. 1A and 1B show photographs of culture plates 100 including growth media 102. The illustrated plates are circular Petri dishes containing medium. Colonies may be grown on different types of media. Media that may be used includes Brain Heart Infusion (BHI) agar, Plate Count Agar (PCA), Tryptic Soy agar (TSA), Luria-Bertini (LB) Agar and Nutrient agar (NA).

The use of automated systems that bring circular Petri dishes into the analysis system allows high throughput and longitudinal analysis for microbial identification. Rotation of plates or plate images to a precise orientation can be used in order to record the exact location of colonies and to re-locate a colony after the Petri dish has been rotated. Barcodes or other rotation fiducials can be placed on Petri dishes or plates. These barcodes can include encoded plate-identification numbers used with electronic lab management systems to manage and cross-reference data collected from various instruments or at various times. Some examples use a side-view camera to read the barcode, a top- or bottom-view camera for visual inspection or targeting or to read the barcode, and the laser to read the diffraction pattern.

The illustrated plates 100 add a fiducial marker on the base of the Petri dish or other culture plate, e.g., a small barcode in a known location on the base. Images of the plate created by an image capture device may be oriented using the fiducial marker. One or both of the images of the plate 100 may be electronically rotated to a known orientation so that any colony can be accessed one or more times for picking or further examination. Mechanical rotation may also be used to change the alignment of a plate 100. Accordingly, a particular colony can be reliably located and repeatedly measured over the duration of an experiment using a particular culture plate, even when that culture plate is rotated during handling (e.g., repeated transfer back and forth between a laser measurement station and an incubator). Alternatively or additionally, coordinates of colonies can be determined by rotation algorithms independently of any rotation of the image data. An output image with colony number or identification can be provided to the user to allow overlay onto the image for colony identification if necessary. The barcode can include an encoded lab-management-system plate identifier (ID). Various barcode formats can be used, e.g., UPC, QR code, or DataMatrix. In some examples, the barcode is not rotationally symmetric. This permits determining the orientation of the barcode and thus of the plate. In some examples, the barcode is arranged on the plate away from a center of the plate in order to improve the resolution of rotation-angle measurements based on the barcode. Various aspects use a plate camera to both read the barcode and provide visual inspection. Various aspects use a plate camera to read the barcode and determine where the laser should be aimed to measure a particular colony, then aim the laser and irradiate the colony to measure the diffraction pattern.

A software-based algorithm can rotate the data set collected electronically. This can be used in place of or in addition to mechanical rotation of the plate before image capture. Reducing the need for mechanical rotation can reduce mechanical complexity of a measurement instrument and time required for each measurement, increasing throughput of a high-volume measurement device. Some examples, however, can additionally or alternatively include a mechanical rotation controlled by the detected barcode location or orientation. This removes the need for manual control of rotation as in some prior schemes. However, in some examples, the plate can be rotated based on the location of the detected barcode.

In various aspects, 1-dimensional (1-D) (104 in FIG. 1A) or 2-D barcodes (106 in FIG. 1B) can be used. The barcodes can be apparent under visible light (e.g., in the 400 nm-700 nm wavelength band) or under light of other wavelength(s). For example, the barcode can be infrared (IR)-fluorescent or IR-absorbing, so that the barcode is apparent under IR illumination. This can advantageously reduce interference between the barcode and visible-light diffraction patterns of colonies growing over the barcode. The barcode may also be designed to absorb light at frequencies other than a frequency of the laser. This prevents the barcode from interfering with scatter patterns created by the laser passing through a colony located above the barcode. A barcode with some redundancy, error-detection, or error-correction (e.g., a QR code) can be used so that the barcode will still be readable even when some colonies have grown over it.

Figure 2:
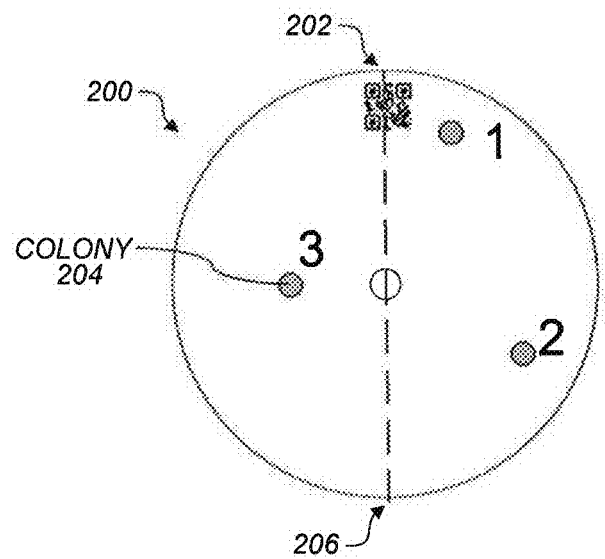
FIG. 2 shows a schematic of a culture plate having three colonies.

FIG. 2 is an illustration of a circular culture plate 200 having a barcode 202 and example colonies 204 (numbered 1-3). The dashed line 206 through the center of the barcode and the center of the plate 200 is a reference for the rotation of the plate 200. The image of the plate can be rotated so that the dashed line 206 in the image has a desired orientation, e.g., vertical or horizontal, when displayed. The dashed line 206 may be observed by a plate camera that is capable of imaging the entire plate. The barcode 20 may be used independent of the dashed line 206 to identify automatically an orientation of the plate 200 from an image captured by a plate camera. In various aspects, the relative positions of the three colonies 204 themselves may be used to determine an orientation of the plate 200. Each colony 204 has a different distance from the center of the plate 200, from the other two colonies, and from the edge of the plate. Analysis of these relationships may provide a reference for identifying orientation of the plate 200. In one aspect, orientation of the plate 200 is used to track the respective colonies 204 on the plate 200. For example, after rotation of the plate 200 the absolute x, y coordinates of colony 2 will change. In order to direct the laser to colony 2, the location of colonies 204 on the plate can be identified and the colony 204 that is the same colony 2 from the earlier image of the plate 200 can be identified. Once new x, y coordinates for colony 2 are determined, the laser may be aimed at colony 2.

In some examples, captured images of a plate are segmented, e.g., using conventional image-segmentation techniques, to locate colonies. Image segmentation is the process of partitioning a digital image into multiple segments (sets of pixels, also known as superpixels). The goal of segmentation is to simplify and/or change the representation of an image into something that is more meaningful and easier to analyze. Image segmentation is typically used to locate objects and boundaries (lines, curves, etc.) in images. More precisely, image segmentation may be implemented as a process of assigning a label to every pixel in an image such that pixels with the same label share certain characteristics.

Once the colonies are located, they can be analyzed over time. However, colonies include living, growing organisms. Accordingly, colonies can change in size or position over time. Colonies can merge, split, grow, shrink, or die between the time a first image is captured and the later time a second image is captured. New colonies can grow in between measurement intervals, e.g., while the plate is in an incubation chamber. Thus, the same plate may exhibit different patterns of colonies at different times.

Inoculant can be applied over substantially the whole surface of the medium in a plate, so colonies can grow at substantially any location on the plate in this example. Inoculant may also be applied directly to a surface of a plate without media so that colonies can be present, at least for the duration of observation, on the plate without media. Colonies present on a "substrate" may thus be present either on media or directly on a solid surface such as a plate or slide.

In various aspects, the colony may be grown until the diameter of the colony is approximately 1 to 2 mm and the diameter of the laser beam on the colony may also be about 1 to 2 mm. The diameter of the colony at the time of analysis may be varied, but, the colony may be grown to a diameter greater than the laser beam. See FIG. 8. The thickness of the colony (along the optical axis) depends on the species, and may be typically about 0.2 mm to 0.4 mm. The substrate and the medium may be substantially transparent to the wavelength emitted by the laser. For example, the media may be an agar media, which provides nutrients and an attachment region for the bacteria colony.

Figure 3:
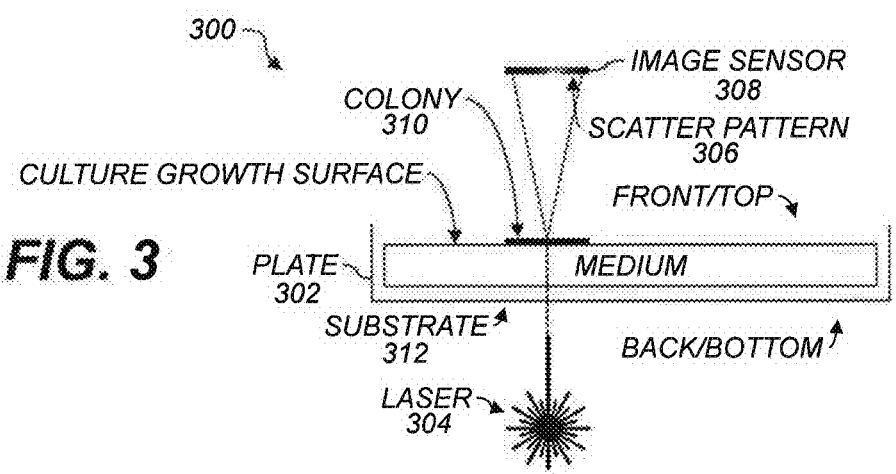
FIG. 3 shows a cross-section of a culture plate having a substrate and a growth medium in the plate according to various aspects.

FIG. 3 shows a schematic side view 300 of a culture plate 302 and imaging components. The laser 304 is shown firing from back to front to produce a transmitted scatter pattern 306 that is captured by an image sensor 308 as a scatter image. The scatter pattern 306 is an arrangement of light indicative of the colony 310 that may be projected onto a surface (e.g., screen, imaging chip, etc.). The scatter image is a recording of the scatter pattern in film, as electronic information (i.e., an image file), or the like. In other implementations (not shown), the laser 304 can shoot from the front/top side to produce a reflected scatter pattern due to the light from the laser 304 reflecting back to an image sensor 308 on a same side of the substrate 312 as the laser 302.

The side view 300 shows a substrate 312 and a medium 314. In some implementations, a colony 310 may be present on the substrate 312 without a medium 314. The plate 302 and the substrate 312 may be formed from plastic, glass, or other material. The substrate 312 is preferably transparent for implementations in which coherent light from the laser 304 passes through the substrate 312 before reaching the image sensor 308. The colony 310 may be grown on the medium 314 using protocols known by one of skill in the art. The growth conditions and the media 314 may vary, depending on the strain of the bacteria or other microorganism. The following list of bacterial species may be grown on a plate 302 described above: Gram-positive foodborne bacterial species including, but not limited to, *Listeria, Staphylococcus aureus, Bacillus* spp, *Streptococcus, Carnobacterium, Lactobacillus, Leuconostoc, Micrococcus, Brocothrix* and *Enterococcus*; Gram-negative bacteria including, but not limited to, *Salmonella, E. coli, Yersinia entercolitica, Serratia, Proteus, Aeromonas hydrophilia, Shigella* spp and *Cirobacter freunddi*.

In some examples, a plate 302 as described herein has any shape, provided it does not have two straight, non-parallel edges—when viewed from above—long enough to permit registration, e.g., >1 cm or >0.25 in. Shapes without such edges are referred to as "non-registrable." Registerable plates allow for tracking the orientation of the plate by its shape alone. Thus, techniques described herein for identifying plate orientation may be unnecessary for registrable plates. For example, a plate 302 described herein, also referred to as a "culture plate," can be substantially circular or substantially oval in shape, or can have only one straight edge with length>1 cm or >0.25 in., or can have at most two straight edges with length>1 cm or >0.25 in., those edges being substantially parallel (as a result of which registration on the straight edges alone does not reliably locate the culture plate with respect to the laser).

In some examples, a system includes top-(front-) and bottom-(rear-) viewing cameras. For example, a front-viewing camera can be used with non-opaque media 314, e.g., non-opaque agar. A back-viewing camera can be used with, e.g., an emissive (e.g., fluorescent) barcode or other barcode visible from behind, e.g., opaque media 314. In some examples, the barcode is placed on, over, or at, or is embedded in, the surface of the plate 302 closest to the media 314. In some examples, the barcode is placed on, over, or at, or is embedded in, the surface of the plate 302 farthest from the media 314. In some examples, a front-view camera can be focused on, e.g., the media-plate interface, e.g., where the barcode is in this example, rather than on the media-air interface, where colonies are. In some examples, optics can be used in the targeting camera that have different focal lengths for different wavelengths (e.g., a front-view camera that focuses visible light at the media-air interface and that focuses IR light at the media-plate or plate-air interface, in examples using an IR barcode). In some examples, the barcode is sufficiently large that it can be read, despite blur, using a camera focused on the media-air interface. The size of the barcode can be selected depending on the focal depth of the camera objective used. In some examples, a barcode is printed on, affixed to, arranged over, etched into, or otherwise disposed at the surface of the plate 302 to which the medium 314 is subsequently applied, and the plate 302 with barcode and medium 314 is shipped, e.g., in a sterile container.

Figure 4:
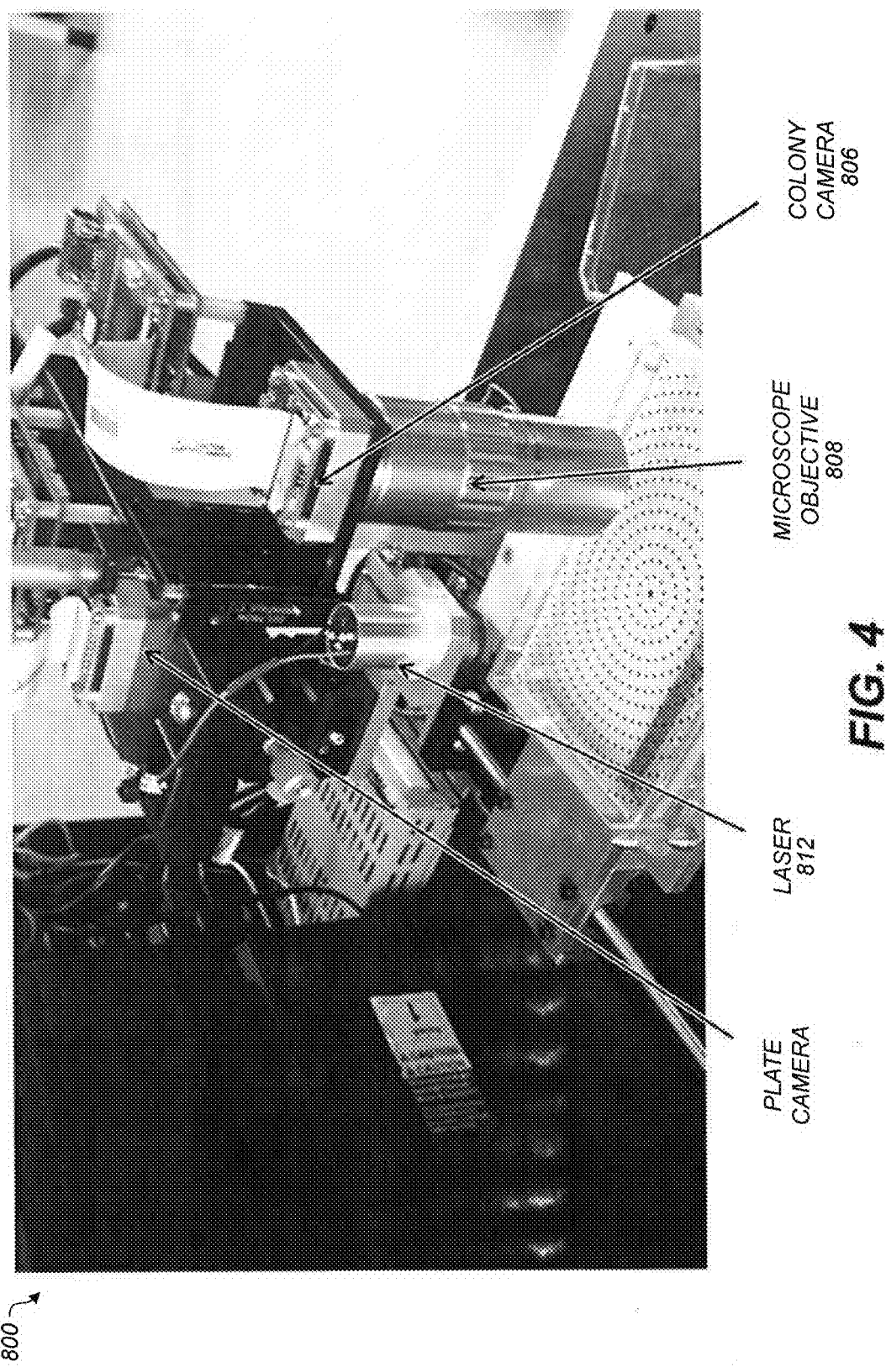
FIGS. 4, 5, 6, and 7 show graphical representations of photographs of imaging equipment according to various aspects.

FIG. 4 shows a photograph of a BARDOT imaging device 400 having a plate camera 402, a coherent light source or laser 404, a colony camera 406, and a microscope objective 408. An optical detector located beneath the plate 410 for capturing light patterns created by the laser 404 is not shown in this view. The optical detector may be film or an electronic imaging device such as a CCD Camera or other array of photodetectors. The microscope objective 408 may allow the colony camera 406 to capture an image of an individual colony. The colony camera 406 may use film, or electronic means such as a charge coupled device (CCD) or complementary metal oxide semiconductor (CMOS), or the like, to record the light image on film, in a memory, or similar device. A light image may include normal scattering or diffraction in the lens or around the shutter or other aperture. The colony camera 406 may be illuminated by ambient light or by a light source below the plate 410 configured to direct light toward the microscope objective 408. In this way, respective laser fingerprints (scatter images) can be collected of individual colonies, and respective light images can be collected of the colonies by the colony camera 406 viewing the colonies through the microscope objective 408. Thus, for each colony there may be two imaging techniques: scatter images generated by the laser 404 and light images via the microscope objective 408. In some implementations, the plate camera 402 and the colony camera 404 may use a same imaging system with the microscope objective 408 serving to change the characteristics of the captured images.

The plate camera 402 may create an image of a whole plate 410 and using computer vision such as edge finding techniques create an x, y map of the plate 410 indicating locations of all the colonies on the plate 410. This map may be used to direct movement of the laser 404 or microscope objective 408 with respect to the plate 410. Due to the additional time needed for moving the plate 410, or microscope objective 408, light images may be captured from less than all of the colonies for which scatter images were captured. Colonies may be selected for additional imaging by a colony camera 406 based on information obtained about the colonies from the scatter images.

A sample holder 412 may also be included between the laser 404 and the optical detector. The sample holder 412 may be sized and shaped for holding the substrate in a position for receiving radiation from the laser 404. The substrate may be provided as a Petri dish. The sample holder 412 may be placed in the system such that light from the laser 404 impinges upon a bacterial colony on the substrate in the sample holder 412. The light from the laser 404 that has impinged on the bacterial colony and is scattered in the forward direction may be detected by the optical detector. The signal from the optical detector may be analyzed by an analyzer and supplied to an output.

The system may be built on an optical board to place each component of the system in the desired position and for controlling moving parts. Additionally, the board may provide vibration isolation. In one embodiment of the present invention, the system may include the laser 404, such as a laser diode having a wavelength of about 635 nm (other wavelengths are also possible), and an x-z moving stage group for holding and moving the laser 404 or the sample holder 412, and thus the substrate and the colony. The system may be configured such that the laser 404, the sample holder 412, the detector may be located on an optical path of the laser 404, in that order. In some embodiments, the distance from the laser 404 to the sample holder 412 may be about 100 mm and the distance from the sample holder 412 to the detector may be about 280 mm. One of skill in the art will recognize that additional distances between the components of the system may be used.

In operation, the bacterial colony and substrate may be placed in the sample holder 412 between the laser 404 and the detector. The laser 404 may generate a collimated beam of light in the order of 1 mm diameter (at the $1/e^2$ irradiance points) that may be directed through the center of the bacterial colony and through the substrate. One of skill in the art will recognize that additional illumination sources and laser beam diameters at the colony may be used within the scope of the present disclosure, as long as a sufficient portion of the colony is illuminated and that the detector receives forward scattered radiation of a sufficient intensity to be detected. Optical elements such as lenses may be present in the optical path between the laser 404 and the detector, but are not shown for convenience. The laser 404 may emit light of any wavelength, optical, infrared or ultraviolet, so long as the properties of the bacteria colony are not substantially altered by the exposure.

Figure 5:
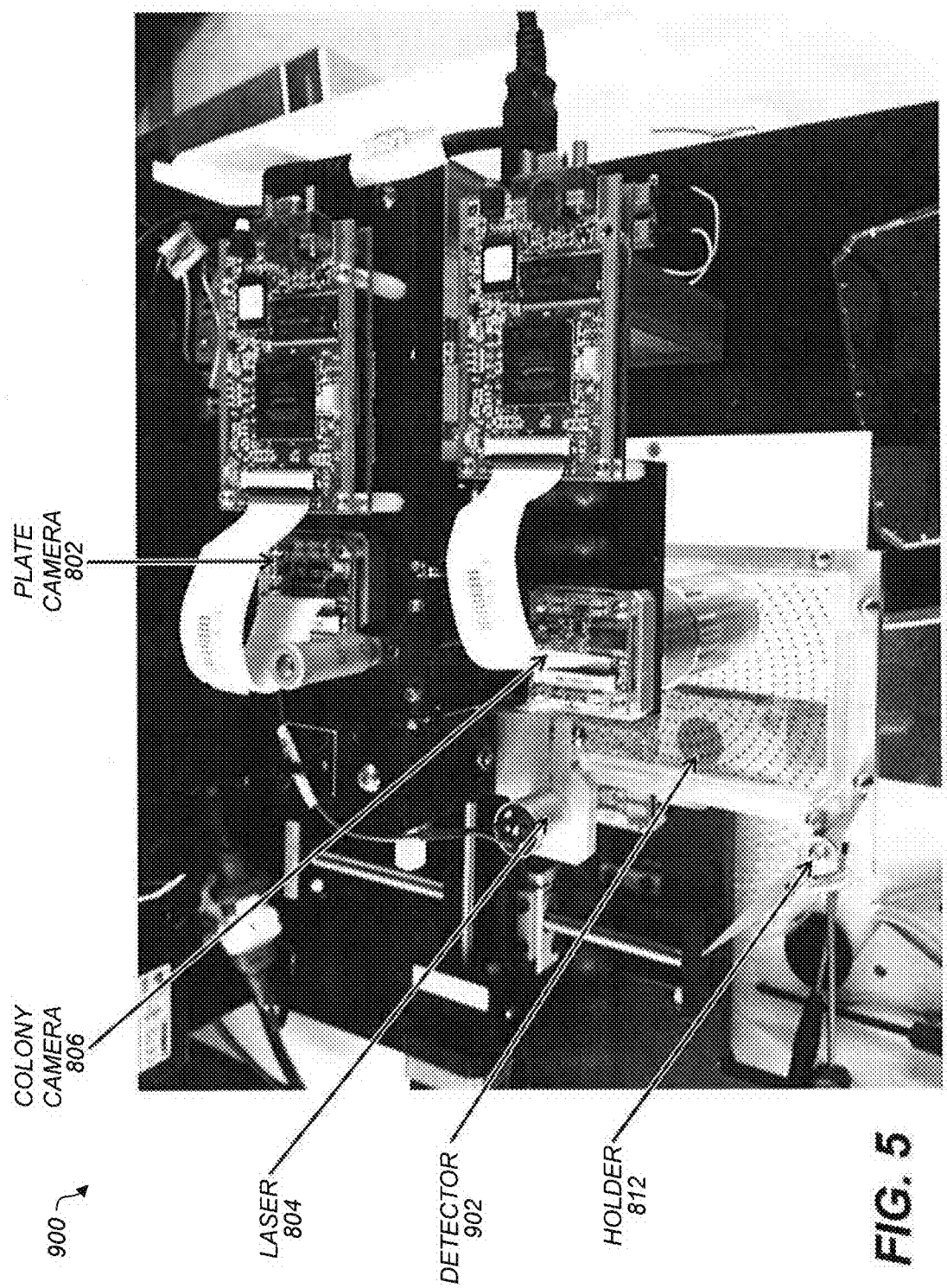

FIG. 5 shows a photograph of a top view 500 of the system. The camera or detector 502 associated with the laser 404 is visible as a black circle underneath the plate.

Various aspects include a plate camera 402 whose coordinates are fixed with respect to, or otherwise in a known relationship with, the laser 404. In an example, the plate camera 402 is laterally offset from the laser 404. The plate camera 402 used to capture an image of the plate as a whole, or substantially the whole of the plate. A system when implemented was able to capture light images in approximately 1 second per colony. In some examples, the colony camera 406 for capturing the additional colony image has the same or higher spatial resolution at the plate than does the plate camera 402. Thus, the colony camera 406 may provide an image of a single colony while the plate camera 402 may provide an image of the entire plate.

The colony camera 406 and the plate camera 402 may generate bright field images. Sample illumination is transmitted (i.e., illuminated from below and observed from above) white light and contrast in the sample is caused by absorbance of some of the transmitted light in dense areas of the sample. Some bacteria have undulating edges and very clear edges. This morphological information is important for classifications and not available from scatter images. The cameras are not limited to bright field illumination. Other suitable imaging techniques for light images include cross-polarized light illumination in which sample contrast comes from the rotation of polarized light through the sample, dark field illumination in which sample contrast comes from light scattered by the sample, and phase contrast illumination in which sample contrast comes from interference of different path lengths of light through the sample. Visual light detected by the colony camera 406 can be modified by filters such as polarization or colors. The filter may be optical filters affecting a characteristic of the light or electronic filters that modify an image after capture. The ability to determine color could be done with filters or it could be done with a color camera.

The holder 412 and any plate inside may be moveable relative to the laser 404, microscope objective, or image capture devices. For example, automated or motor driven adjusting devices such as a three-axis stepping motor may be used to orient the laser location, the microscope objective location, and the like, may be incorporated in the apparatus. The system may be automated such that, for example, a user places a sample in sample holder and the system moves the sample (e.g., with an automated x-y stage), illuminates the sample using the coherent light source, positions the microscope objective on an optical path between the sample and the colony camera 406, analyzes the scatter image, and tabulates, displays, or otherwise provides the results to the user without the need for manual intervention.

Figure 6:
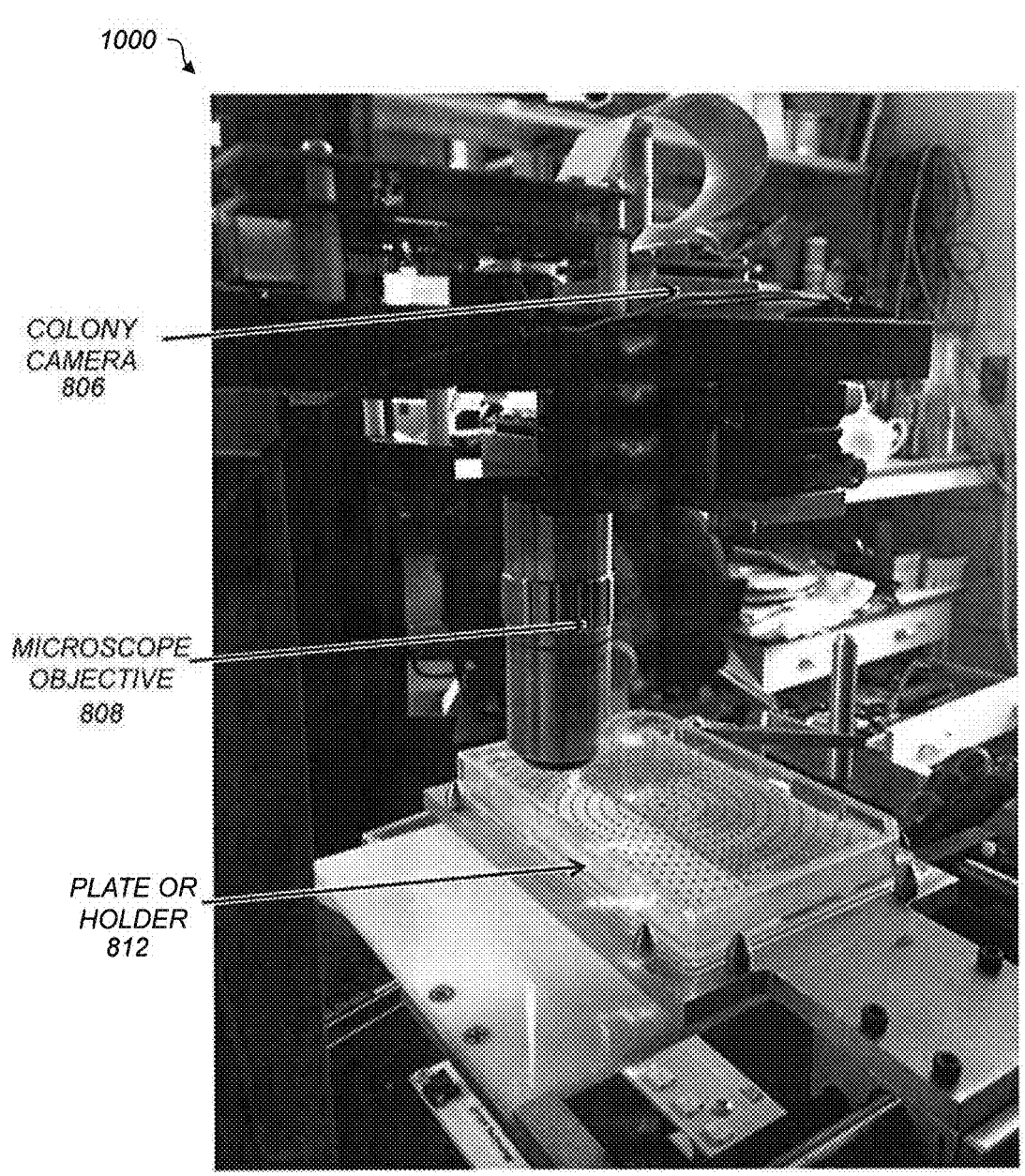

FIG. 6 shows a photograph of the microscope objective from a side view 600. Some examples include a colony camera 406 configured to image the colony from the front of the plate; some examples for use with transparent agar include a colony camera 406 configured to image the colony through the back of the plate (not shown).

Some examples include multiple light sources of different wavelengths or spectral power distributions (SPDs) to collect reflected or back-scattered light. This can permit obtaining additional information regarding colonies. For example, some colonies respond differently to different wavelengths of light. Light images under different SPDs light can be captured using any combination of one or more cameras, one or more optical filters, and one or more light sources. In some examples, colonies are stained and a wavelength is selected to cause the stain to fluoresce. In some examples, colonies are grown on a differential agar that changes color in response to specific chemical reactions carried out by microbes. The light image can then indicate whether that reaction is taking place. The SPD of a light source can be selected to improve contrast of specific colors of a differential agar. For example, blood agar turns from red to clear in the presence of reactions that break down red blood cells in the agar. Mannitol salt agar turns from pink to yellow in the presence of fermentation of the alcohol mannitol.

Figure 7:
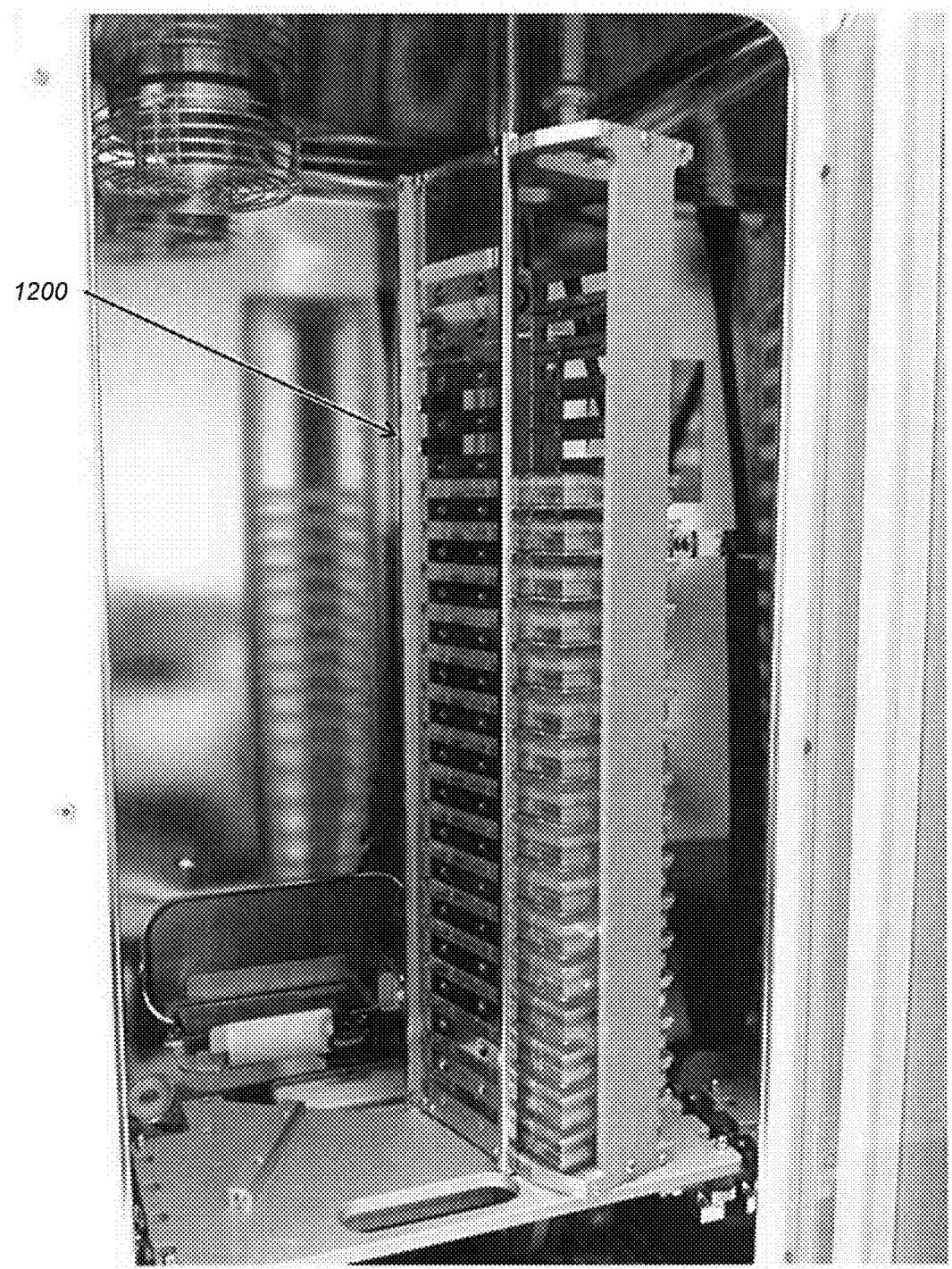

FIG. 7 shows a photograph of an example automated incubator rack 700 containing multiple palates. A plate from the rack of plates may be automatically sent to the detection instrument for analysis at different times and then replaced into the incubator. If the plates are non-registerable plates, each instance of placing one of the places in the detection instrument may result in the place being located at a different orientation with respect to the components of the detection instrument. Various aspects permit the random selection of non-registrable plates from an automated incubator, or holding rack for placement onto an analysis platform such as the Bardot technology, or any other image processing system without the need to physically rotate the plates to a precise location. Thus, as a part of automated analysis, techniques for correlating orientation of a plate from a first time to a second time are useful for maintaining the ability to locate a same colony when the plate is at different orientations.

Figure 8:
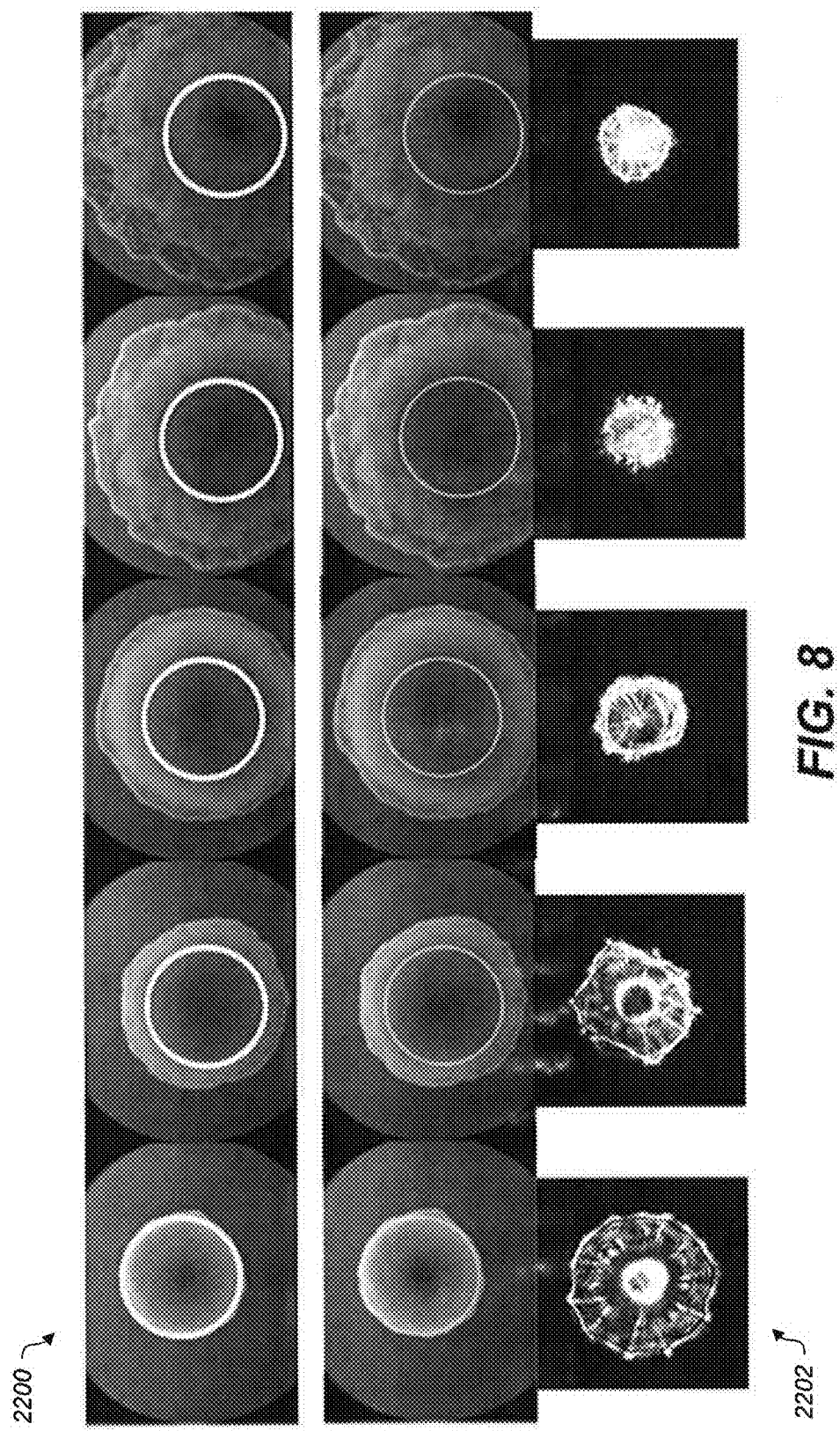
FIG. 8 shows graphical representations of example camera images and scatter images of various colonies.

FIG. 8 shows examples of the size of the laser beam (circular ring) superimposed over visible light images 800 (bright field) of five colonies. The ring is for illustration purposes and does not necessarily imply that the laser may illuminate a colony at the same time the colony camera is capturing an image. Below each pair of light images 800 is a corresponding scatter image 802. In this example, the area covered by the scatter image 802 is inversely correlated with the area covered by the colony in the visible light image 800. This illustrates the increased amount of information available about a colony when both scatter images 802 and light images 800 are captured. The additional information may be used by machine vision and/or machine learning techniques to better identify or classify the colony.

Illustrative Image-Analysis Techniques, e.g., Applicable to a Time Series of Images Growth and change in colonies may be studied over time. For example, a plate with bacterial colonies may be removed from an incubator and imaged by a Bardot system at intervals of 6, 7, 8, 9, 10, 11, 12, 14, 15, 16 hours. This produces a time course of images, both scatter images and light images, that when considered as a time course may provide more information about the bacterial colonies than examination of the various images separately. Two different bacteria species may have similar scatter pattern "finger prints" at some time points, but have different changes in the respective scatter patterns over time. Therefore, comparing changes in the scatter patterns over time may be sufficient to distinguish the two bacteria species from each other. Times associated with images, scatter images or light images, may be additional information that can be provided to a database of images for use in classification of images by machine learning. Thus, instead of training a machine learning system with a scatter image of E. coli, the training data could include a specific scatter image of E. coli after six hours of incubation.

Figure 9A:
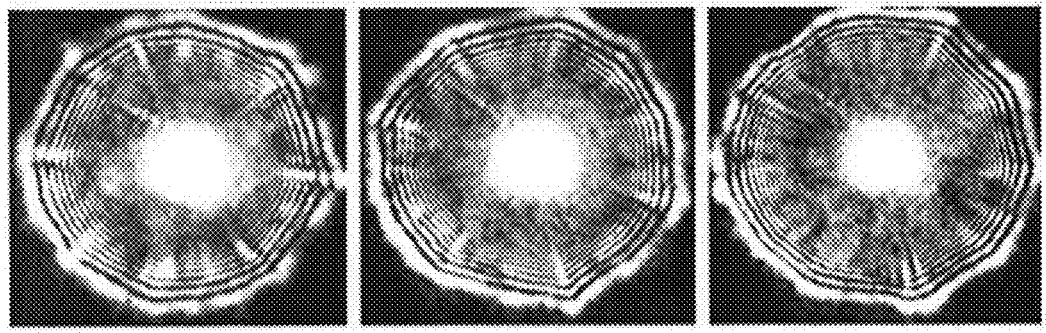
FIGS. 9A and 9B shows graphical representations of scatter images of a colony over a time course.
Figure 9A:
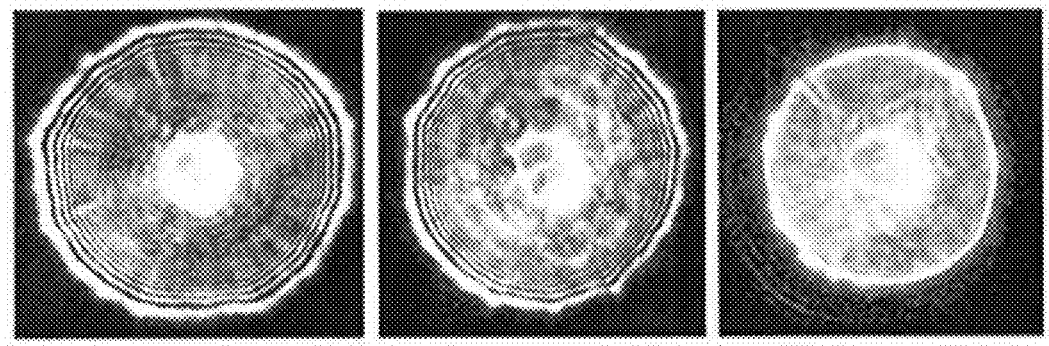
Figure 9B:
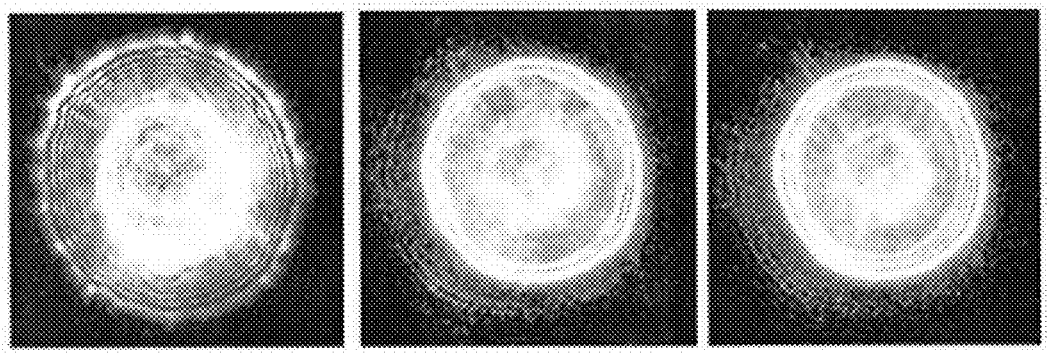
Figure 9B:
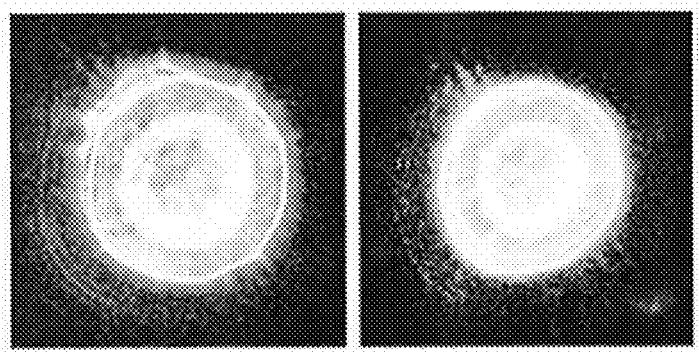

FIGS. 9A and 9B show graphical representations of scatter images of an example time-based analysis of a single tested bacterial colony. Scatter images are shown in FIG. 9A for times from 13 hrs, 5 min to 23 hrs, 3 min and in FIG. 9B from 25 hrs, 7 min to 32 hrs, 26 min. As shown, the scatter pattern of the colony changed over time even though the colony, substrate, and media remained the same. That change is made more apparent by aligning the scatter images in order of time (e.g., image time stamps). In order to perform this and other time-based analysis of multiple colonies, techniques described herein can be used to correlate colony images over time. An image can include, e.g., >20 colonies of microbial organisms. A series of images of a same colony over time may include 2, 3, 4, 5, 10, 15, 20, or more images from different time points.

Figure 10A:
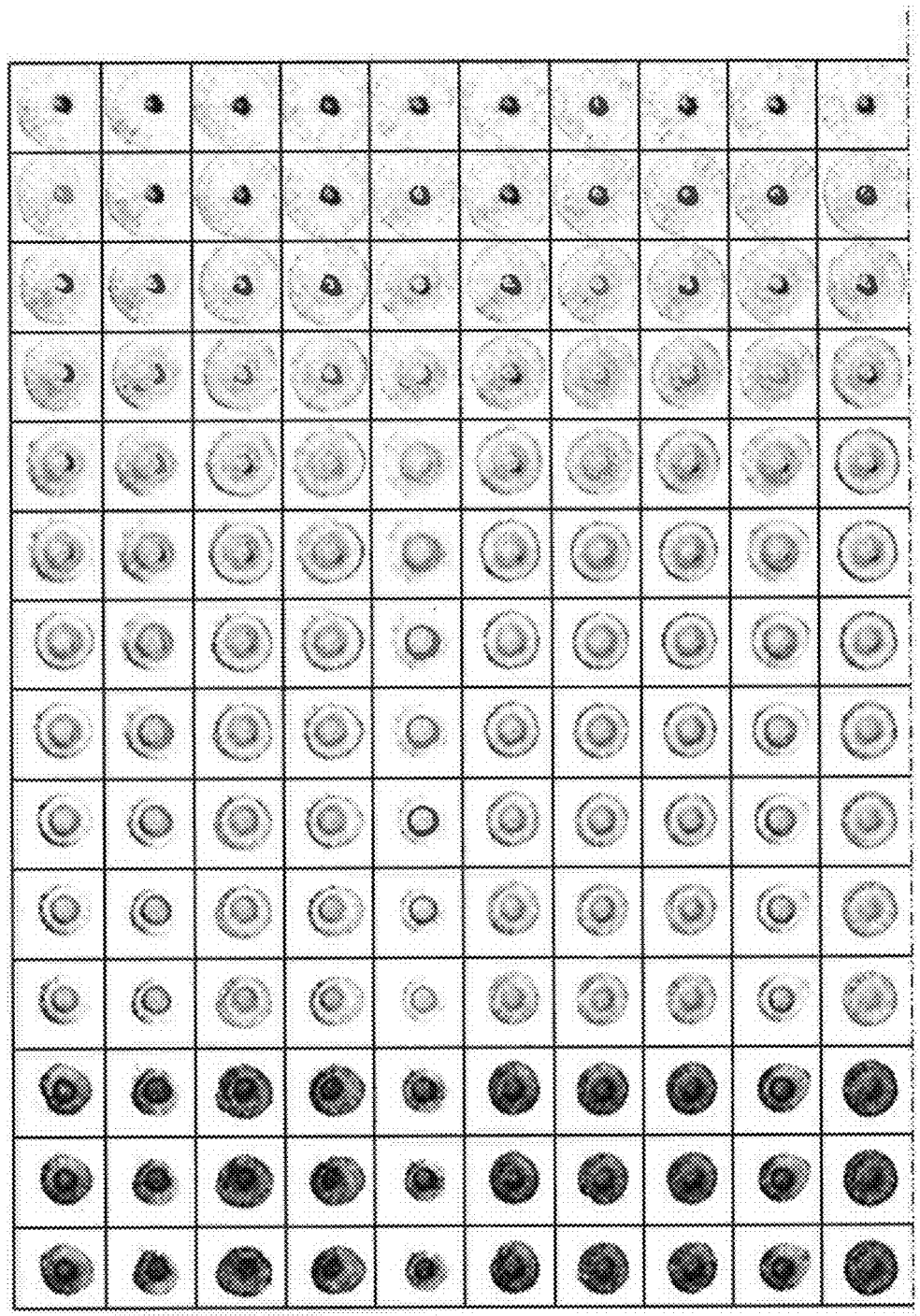
FIGS. 10A and 10B show graphical representations of scatter images of colonies on a culture plate at various times.
Figure 10B:
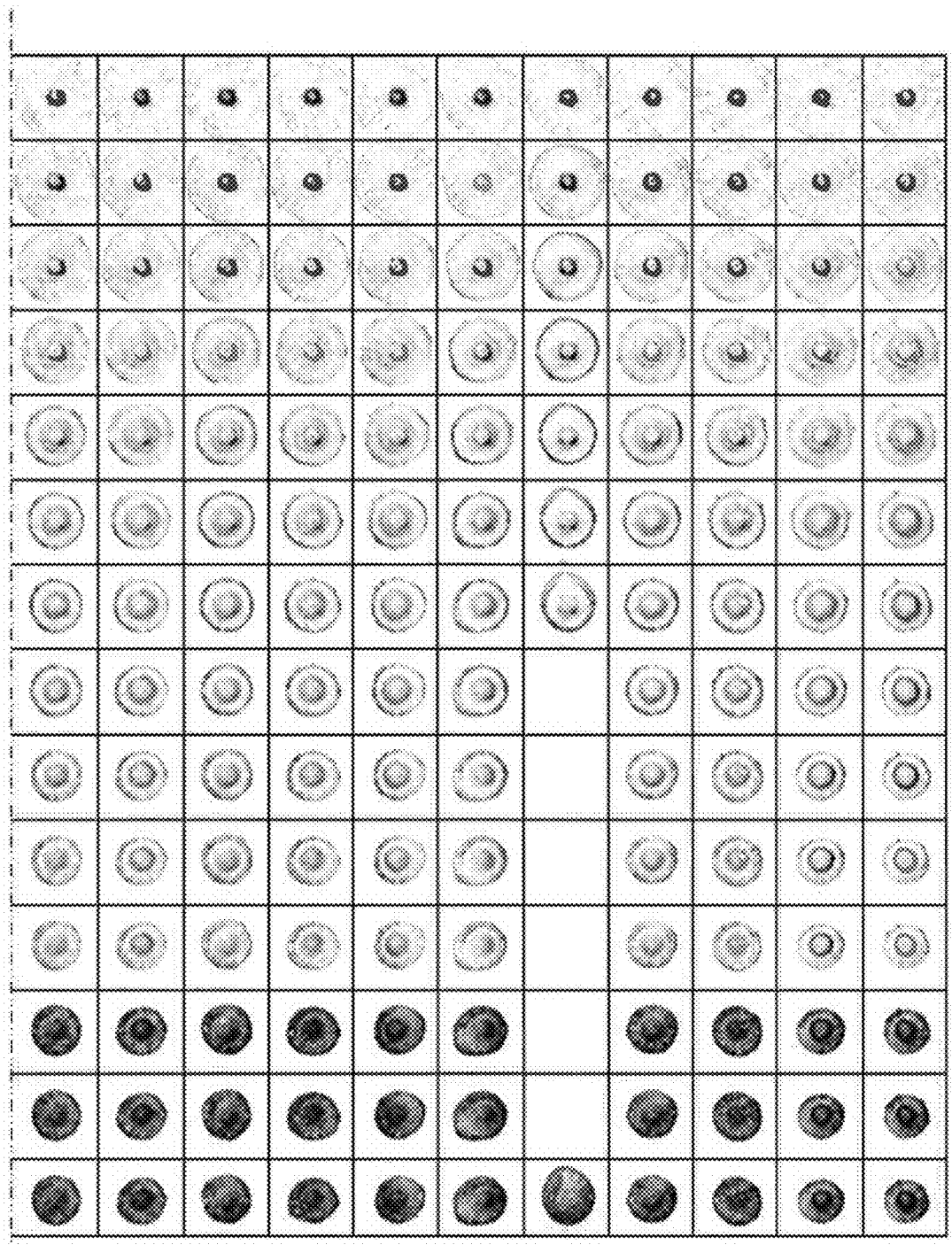

FIGS. 10A and 10B show a time series of scatter images for several colonies. Each column represents a particular colony. Time increases from top (larger images) to bottom (smaller darker images). The similarity in changes across columns shows a similarity in how different colonies change (as measured by scatter patterns) over time. The blank positions in one column on FIG. 10B indicate that the original colony cannot be definitively identified at that time point or it may have been two colonies that are no longer identified as a single colony (e.g., by roundness or similar criterion).

Figures 11, 12:
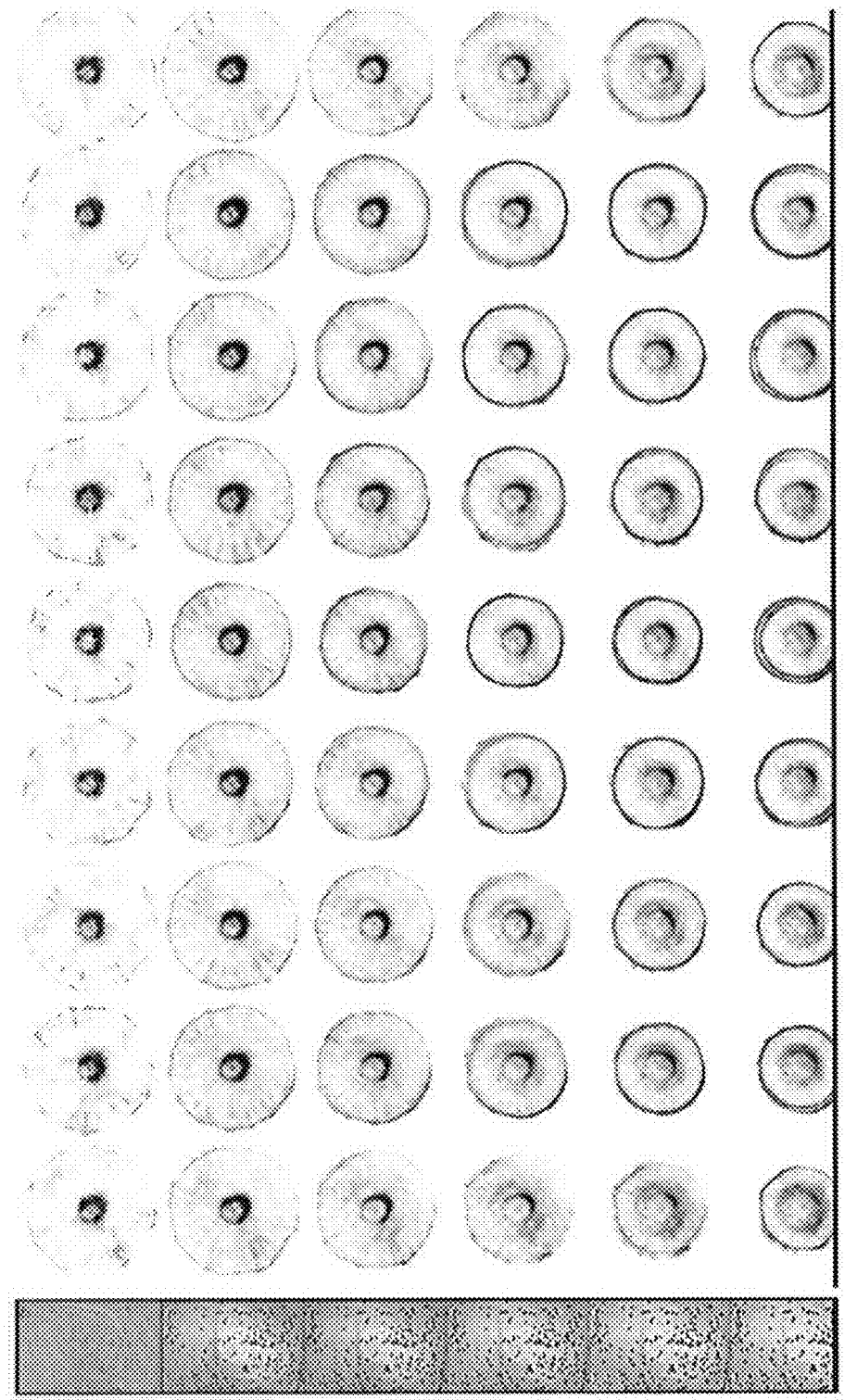
FIG. 11 shows graphical representations of photographs of a culture plate at various times.
FIG. 12 shows graphical representations of scatter images of colonies on the culture plate of FIG. 11 at the various times.

FIG. 11 shows a graphical representation of photographs of an entire (or substantially all) plate at different times. Time increases from top to bottom in FIG. 11 and in FIG. 12. A rectangular plate was photographed. The graphical representations have been inverted (black/white) and their contrast has been adjusted to improve visibility of the colonies (black dots). As can be seen from examination of FIG. 11, the number of bacteria colonies on the plate increases with time.

FIG. 12 shows graphical representations of scatter images of an example time based analysis of multiple colonies on the plate of FIG. 11. The rows (times) correspond to the rows (times) in FIG. 11. Due to optimization, it is possible to image a colony in less than two seconds (including travel time) so imaging 100 colonies may take less than three minutes.

In various aspects, first and second plate images are received, captured, retrieved from memory, or otherwise acquired. The images are segmented, e.g., using edge-finding techniques in the image-processing art, to determine center or other representative coordinates of individual colonies in each image, e.g., for each colony or a subset of colonies. Air bubbles or other features that stand out in the image can also be detected. For many microbes, colonies are generally circular. Colonies can be detected, e.g., based on roundness (e.g., major/minor axis ratio of a best-fit ellipse) of areas having high contrast with the background. Segmentation can include performing a histogram of the image and setting a threshold for colony/non-colony between the two highest peaks of the histogram.

Pairwise distances between the coordinates of the colonies in the first image and the coordinates of the colonies in the second image are then computed. Mathematical optimization, e.g., least-squares minimization, is then used to select the pairwise distances that result in a lowest overall total distance, or a distance meeting selected criteria (e.g., no distance>X, all distances<tolerance Y, for some X or Y). The selected pairs indicate which detected colonies are the same. The same colony is group of microorganism that all came from a same parent organism and have continuous and contiguous growth. Thus, even if the population of cells in a colony completely turns over in a number of hours it is still referred to as a "same" colony. An example is shown in Table 1.

TABLE 1

| Image 1 | Detected colony coordinates | Image 2 | Detected colony coordinates |
| --- | --- | --- | --- |
| 1A | (1, 2) | 2A | (2, 2) |
| 1B | (10, 20) | 2B | (31, 42) |
| 1C | (30, 40) | 2C | (11, 20) |

The lowest total pairwise distance is 1A-2A, 1B-2C, 1C-2B, so those three pairs are identified as representations of three respective colonies. Once the colonies are determined, scatter images can be analyzed in a time series.

In some examples, an objective function F is mathematically minimized. Let $D_{ni}$ be the coordinates of item n $\in$[1, N] detected in image i. (e.g., n$\in$[A, B, C] and i $\in$[1,2] in Table 1). F can be then defined as:

$$F = \sum_{i=1}^{N} \min_{j \in [1,N] \neq i} dist(D_{j1}, D_{j2}) \qquad (1)$$

with dist between two coordinates represented as vectors D and E being:

$$dist(D, E) = \begin{cases} |D - E| & \text{if } |D - E| > \text{tolerance} \\ 0 & \text{otherwise} \end{cases} \qquad (2)$$

for a selected tolerance.

In some examples, if two colonies are determined to be touching, e.g., having representative coordinates within a selected distance of each other, they can be disregarded in future analysis since such colonies may not have a useful scatter pattern.

In some examples, images of a particular colony over time are inspected. If a colony does not change size over time, it can be determined to be a bubble, not a colony. A time series also permits determining which organisms grow relatively earlier and which grow relatively later. This information can be used in identifying the organism(s) in a particular colony. Time series of light images also allow for calculation of growth rates of colonies.

In some examples, each pair of images can be processed individually as described above. In some examples, for image pairs after the first, past coordinates can be adjusted. Let $C_{ci}$ be the coordinates of colony c in image $i \in [1, \ldots]$. Then for images 1 and 2, $C_{c1}$ and $C_{c2}$ can be compared. For images n and n+1, $C_{cn}$ and $C_{cn+1}$ can be compared. Alternatively, $C_{cn+1}$ can be compared to $\langle C_{c\ n-1}, C_{c\ n} \rangle$, with $\langle \bullet, \bullet \rangle$ representing, e.g., an arithmetic or geometric mean. $C_{cn+1}$ can be compared to $\langle C_{c\ n-k}, \ldots, C_{c\ n} \rangle$, $k \in [1, n-1]$. This can reduce sensitivity to small position changes such as those due to removal of a plate from the imaging system and replacement of the plate in the imaging system. Such changes can be due to translational or rotational position errors of the plate within the tolerances of the plate-handling system, or to slight variations in image intensity that cause, e.g., histogram peaks to fall in different pixels on subsequent exposures.

Illustrative Image-Analysis Techniques, e.g., Applicable to Individual Images

Various example techniques herein evaluate the scatter patterns collected using the BARDOT technology and separate different colonies based on a variety of features, e.g., morphological features. Various aspects make a determination of the possible groups of colonies on a particular plate without having to go through an identification process. These "colony differentiators" give the user an idea of how many different phenotypes may be present on a particular plate. Each subgroup can be visually identified on a map of the plate or visually marked by color. It is also possible to use this differential technique to create a classification for this "unknown" set of organisms to be placed within a database system for future recognition. This permits determining the prevalence of a certain type of organism in a sample.

In some tests using culture plates, it is desirable to know the number of different types of organisms on a plate independently of the specific identities of those organisms. For example, there may be common, non-pathogenic bacteria in the samples. To find samples with pathogens or samples with a greater likelihood of a pathogen, the number of groups can be used. This can permit selecting samples based on indicator organisms, which non-pathogenic organisms that tend to occur along with pathogens. For example, in a hamburger sample, a harmful bacterium and a non-harmful indicator bacterium may generally grow together. In another example, if meat-processing equipment is not cleaned properly, a pathogen and a non-pathogen may occur together.

The values of the moment invariants (features) may be represented by a vector of features (scalar values) extracted from the image and then compared with criteria established by training an recognition algorithm with known data sets so as to identify the genotype of an organism or the properties of the organism, such as pathogenicity. If identification of an colony is not possible or not necessary, similar information from images of the colony may be compared with other colonies on a substrate to identify an number of different colony types present.

In some examples, if the number of groups (the number of different types of organisms) on a plate is not the number expected (e.g., the number inoculated onto the plate), the plate can be selected for further investigation. This can permit performing relatively time-consuming or expensive tests, such as PCR tests, only on plates more likely to be relevant, or only on colonies more likely to be of interest. Such a situation can arise, e.g., due to contamination or sub-culturing of different samples. Samples may be observed at a series of time points using the techniques discussed above. Changes in the detected number of groups, either an increase or decrease, may cause the system to generate an alarm or message notifying a user of the change.

In some examples, light images (as used herein, images captured under incoherent illumination, e.g., IR, visible, or UV) or scatter images can be captured of one or more colonies on a plate. Features can be determined from those images. The colonies can be clustered in feature space. The number and combination of features can be selected for each clustering, e.g., based on the expected types of organisms, to increase the accuracy of the clustering. Histogram equalization or other contrast- or tonescale-adjustment techniques can be used in determining features of light images or scatter images.

A variety of feature extraction algorithms may be used, either individually or in combination so as to characterize an image. Scatter images of the colony may exhibit generally circular symmetry, and algorithms such as Zernike and Chebyshev moments may be used. As the scatter images may also exhibit textures, and another set of characterizing data may be obtained using so-called Haralick texture features. Light images may be analyzed similar to scatter images. If features extracted from scatter images are insufficient to group a set of colonies, features from light images may additionally be used.

Example features include morphological features of light images, e.g., size, shape, or color, or morphological characteristics evident in a time series of light images, e.g., growth rate or movement. Example features include morphological features of scatter images such as texture, Fourier transform, principal components, Zernike polynomials, Walsh-Hadamard transform coefficients, wavelet transform, or other transform coefficients, or the magnitudes or arguments thereof. Other features can alternatively or additionally be used.

In an aspect, the scatter images or light images may be characterized by applying a azimuthally invariant orthogonal moment technique, such as that known as a Zernike moment invariant, to obtain a vector characteristic of the sample. Generally, lower-order Zernike moments quantify low-frequency components (which may be considered as "global characteristics") of an image and higher-order moments represent the high-frequency contents (which may be considered as "fine details"). Therefore, there is always a tradeoff between the desired level of image details that can be analyzed, and the order of the moments to be used. A $20^{th}$ order analysis yields a vector having 120 components. Images may be translated so that the center of the scatter pattern is at the center of the image. To compute the Zernike moments of a given image, the center of the image is taken as the origin and pixel coordinates are mapped to the range of the unit circle.

The magnitude of a Zernike moment is azimuthally invariant, so that the effect of azimuthal variations of the image are minimized. Other similar analytical techniques, such as discrete Krawtchouk or radial Chebyshev polynomials or continuous pseudo-Zernike polynomials may be used, and may be adapted to similar analytical use.

As with all digital data processing, the resolution of the image, the granularity of the calculations and the accuracy of the numerical analysis algorithms are chosen as a balance between accuracy, noise generation, memory capacity, computation speed and the like, and differing parametric values and specific analytic techniques may be chosen by persons skilled in the art to perform the functions of the method and system disclosed herein.

For example, texture features can include Haralick features for one of the four Haralick co-occurrence matrices computed over a light image or a scatter image. The basis for these features is the gray-level co-occurrence matrix. This matrix is square with dimension Ng, where Ng is the number of gray levels in the image. Element [i,j] of the matrix is generated by counting the number of times a pixel with value i is adjacent to a pixel with value j and then dividing the entire matrix by the total number of such comparisons made. Each entry is therefore considered to be the probability that a pixel with value i will be found adjacent to a pixel of value j. Since adjacency can be defined to occur in each of four directions in a 2D, square pixel image (horizontal, vertical, left and right diagonals four such matrices can be calculated. The texture features may be the one or more of angular second moment, contrast, correlation, variance of sum of squares, inverse difference moment, sum average, sum variance, sum entropy, entropy, difference variance, difference entropy, first or second measures of correlation, or maximum correlation coefficient. Texture features can also or alternatively include number of gray levels or distance for the co-occurrence matrix.

For example, Fourier-transform features can include the relative or absolute magnitudes or frequencies of peaks, e.g., the first N peaks for a selected N. The peaks can be sorted by amplitude of power ($Im^2+Re^2$) before selecting the first N.

Selection among extracted scatter image and light image features encompasses tradeoffs between desired properties. For example, a higher order of moment invariant provides more sensitivity but also makes the features more susceptible to noise. Therefore, feature reduction may be performed to select the most distinctive features. Feature reduction may be divided into categories: feature selection, in which features carrying the most information are picked out through some selection scheme, and feature recombination, in which some features are combined (e.g., with different weights) into a new (independent) feature.

The dimensionality of the feature vector of the Zernike moments obtained may be reduced by techniques such as principal component analysis (PCA), non-linear iterative partial least squares (NIPALS), stepwise discriminant analysis (SDA) or other similar methods in order to plot the data in a two or three dimensional form and to visualize data clusters representing different bacterial colonies.

Once the features are computed for images of various colonies, the clustering can be perform as known in the machine-learning and statistical art. For example, parametric techniques such as k-means clustering can be used, and different values of k can be tested to find a clustering having residual errors or other goodness-of-fit indicators meeting selected criteria. Parametric techniques require a number of clusters to be set, but generally the question in this application is identifying the number of clusters. Thus, different values of k are tested (e.g., k=2, . . . , k=50) and the clustering results compared to see which value for k formed the most compact clusters.

Nonparametric clustering techniques, such as Bayesian models, do not consider cluster centers per se (thus no need for defining a number of clusters in advance) but rather evaluate separation between clusters and attempt to maximize probability of assignment to a group. A predetermined separation can be defined but the number of groups does not need to be defined. Hierarchical tree clustering ("hierarchical clustering") can also or alternatively be used. In some examples, hierarchical clustering operates by progressively grouping colonies having similar properties (nearby in feature space). In some examples, hierarchical clustering operates by dividing the feature space into clusters using another clustering algorithm, e.g., k-means, and then dividing each resulting cluster using the other clustering algorithm. Hierarchical clustering produces a tree structure, e.g., a dendrogram, showing the relationships between larger clusters and their constituent smaller clusters. Clusters at any level can be selected, e.g., based on a number of clusters at that level compared to a number of expected organisms, or based on how well separated the clusters at each level are. Mean-shift clustering can also or alternatively be used. Clustering can be performed in feature space, providing an indication of the number of types of organisms on a plate without requiring the types themselves be determined.

The feature vectors may be clustered by unsupervised machine learning methods such as K-Mean clustering, Ward's hierarchical clustering, Kohonen's self-organizing maps or similar methods. The feature vectors may be also classified by supervised learning methods such as linear or quadratic discriminant analysis (LDA, QDA), neural networks (NNs), or support vector machines (SVM).

SVMs are based on decision hyperplanes that define decision boundaries. An optimal decision hyperplane may be defined as a decision function with maximal margin between the vectors of two classes. SVMs are a set of related supervised learning methods used for classification and regression. They belong to a family of generalized linear classifiers.

A property of SVMs is that they simultaneously minimize the empirical classification error and maximize the geometric margin; hence they are also known as maximum margin classifiers.

Support vector machines map input vectors to a higher dimensional space where a maximal separating hyperplane is constructed. Two locally parallel hyperplanes are constructed on each side of the hyperplane that separates the data. The separating hyperplane is the hyperplane that maximizes the distance between the two locally parallel hyperplanes.

In some examples, an additional colony image is captured. The additional colony image can be a light image from which features can be extracted resulting in additional identification parameters. The colony image can be recorded and associated with the laser scatter pattern of that colony and saved, e.g., in a database. Various aspects permit identification of the populating organism in a colony for very small colonies, e.g., less than 150 microns in mean diameter. For example, colonies that are smaller than the diameter of the laser beam may produce a weak scatter signal. The light image can be used to analyze such colonies. Moreover, the light images can be used to distinguish colonies from dust specks or bubbles.

The addition of features extracted from light images of colonies can improve speed or accuracy of colony identification compared to identification based solely on scatter images. Example features can include colony, color, area, height (e.g., determined using a stereoscopic camera), volume, roughness, and edge/perimeter/contour length, roughness, or fractal dimension.

This technique increases the detected feature set thus providing an increased amount of data for analysis. Various aspects permit analyzing small colonies in an automated fashion.

In view of the foregoing, various aspects provide improved measurement of colonies and identification of colonies on a culture plate. A technical effect is to determine the composition of small colonies. A further technical effect is to present a visual representation of the state of the imaging system, e.g., the organisms composing colonies on the plate, on an electronic display.

Figure 13:
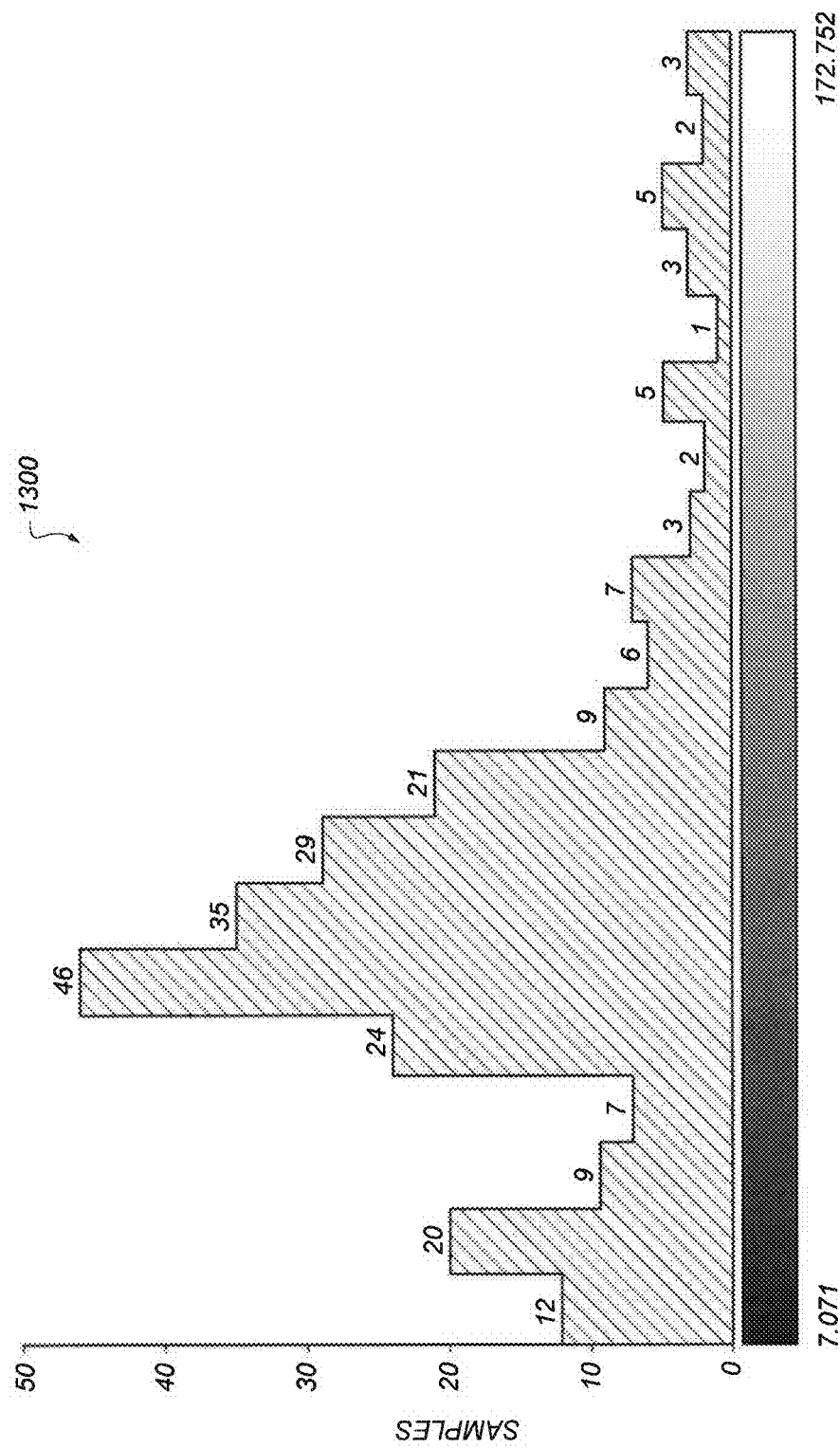
FIG. 13 shows an example histogram of values of a feature.

FIG. 13 shows an example histogram 1300 of perimeter of clusters on a plate. Of 249 samples measured, the statistics were as in Table 2.

TABLE 2

| Count: 249 | Min: 7.071 |
|---|---|
| Mean: 63.049 | Max: 172.752 |
| StnDev: 33.602 | Mode: 48.491 (46) |
| Bins: 20 | Bin width: 8.284 |

The histogram of FIG. 13 may be generated by any of the clustering techniques described above.

Figure 14:
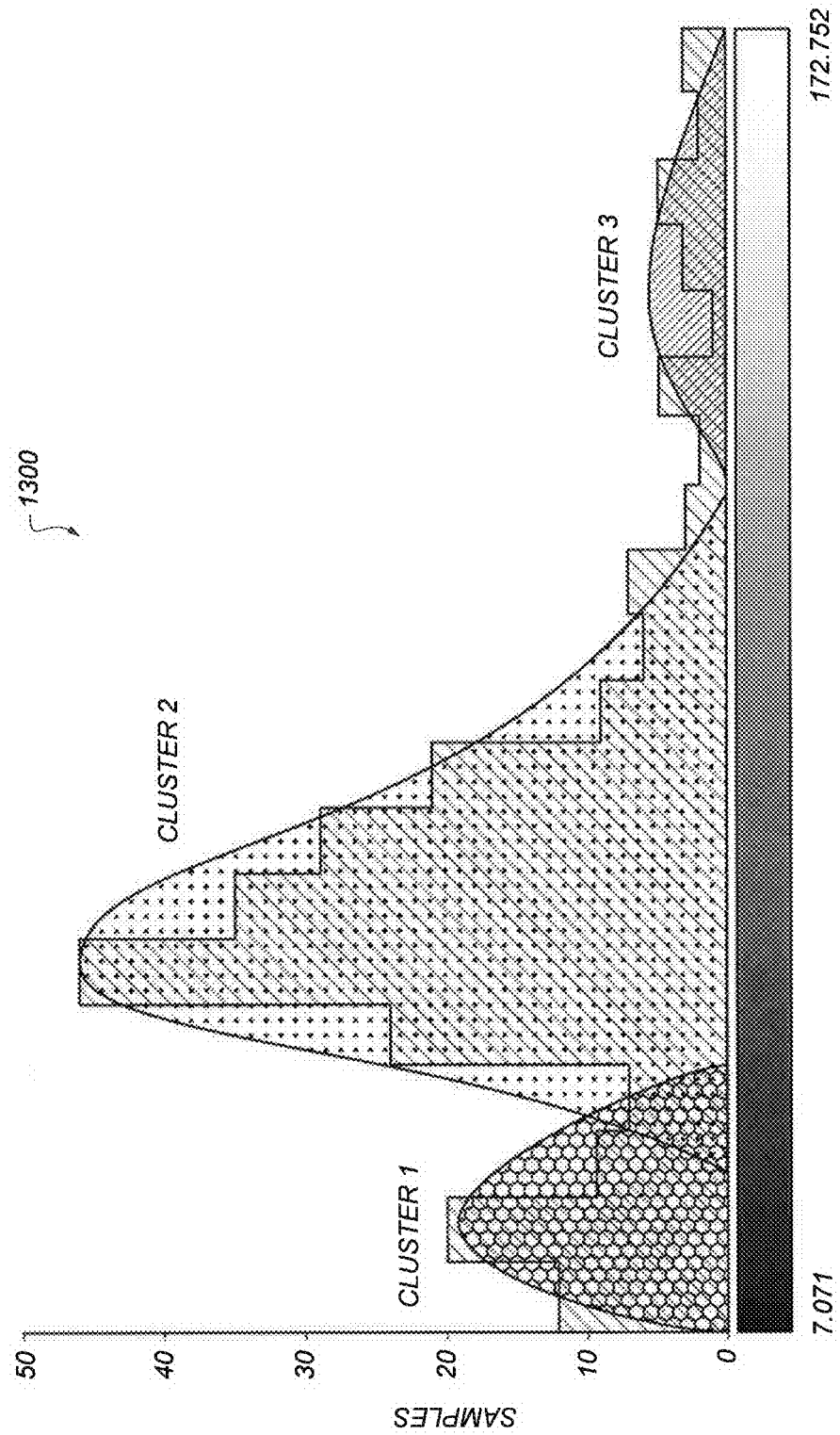
FIG. 14 shows an example assignment of clusters to the values shown in FIG. 13.

FIG. 14 shows the histogram 1300 of FIG. 13 with three clusters (histogram peaks) identified. This can be, e.g., the output of a k-means clustering with k=3.

Figure 15:
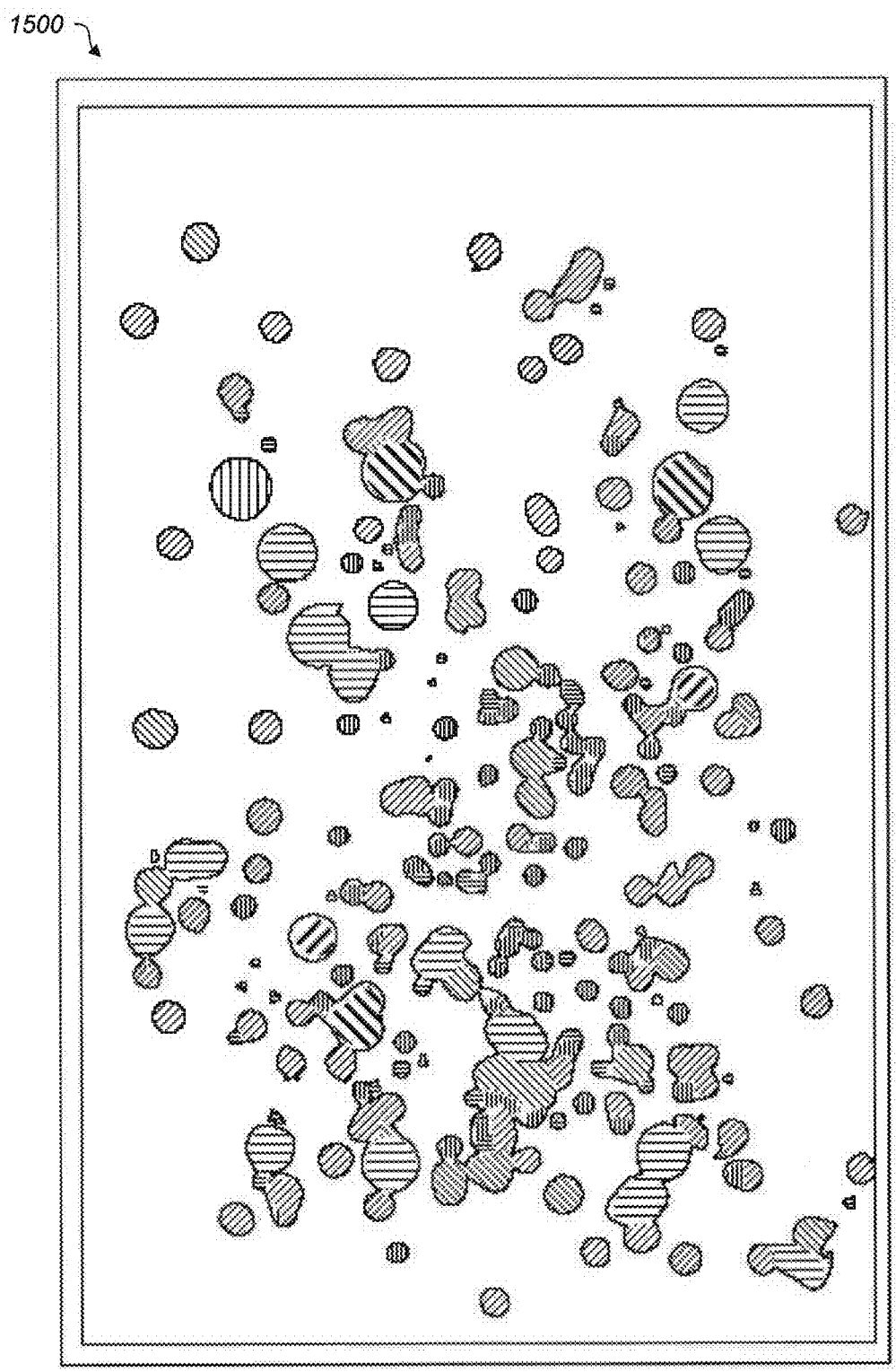
FIG. 15 shows an example cluster map.

FIG. 15 shows an example colony map 1500 of a rectangular plate exhibiting differential selection of colonies based on certain criteria. Each texture pattern corresponds to a "cluster" of organisms (colonies) that are considered to be similar based on analysis of the features used for classifying or categorizing organisms. One method of categorizing is separation based on a single feature; another method is separation based on a combination of features. Once the individual organisms have been classified, the colony map may be created by assigning color or another type of marker to each of the colonies according to the respective classifications. Colors or other types of markers are representative only and have no inherent meaning.

Figure 16:
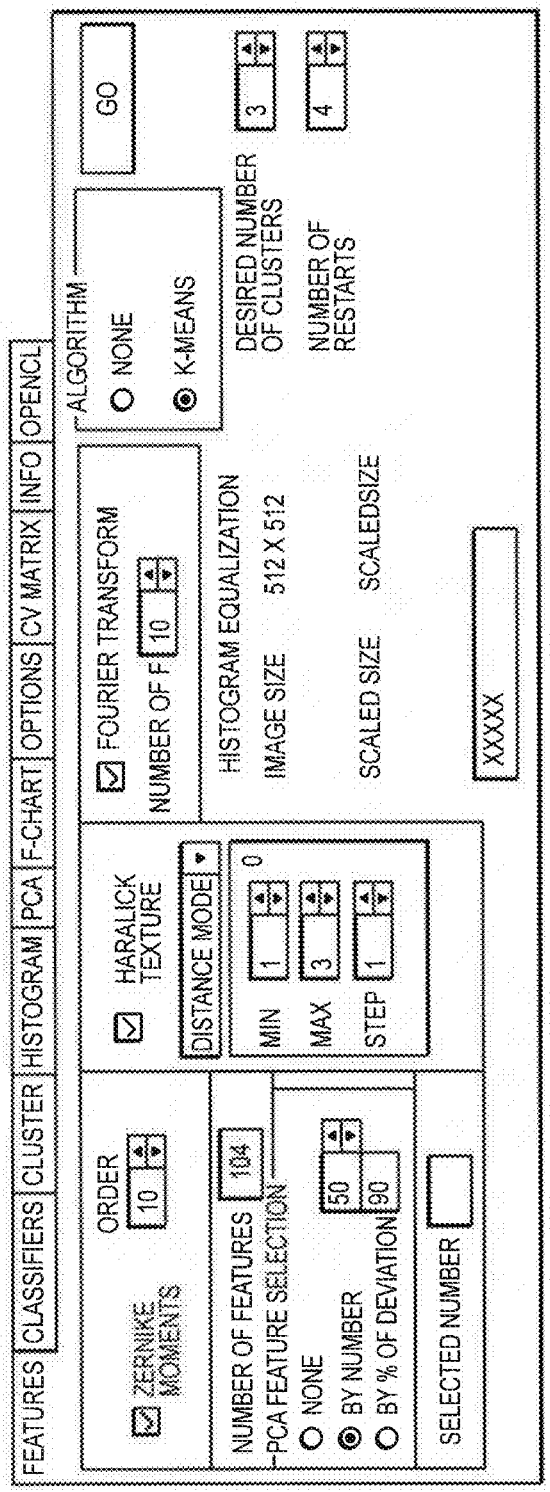
FIG. 16 shows a graphical representation of an example user interface for specifying clustering parameters, and some example parameters.
Figure 17:
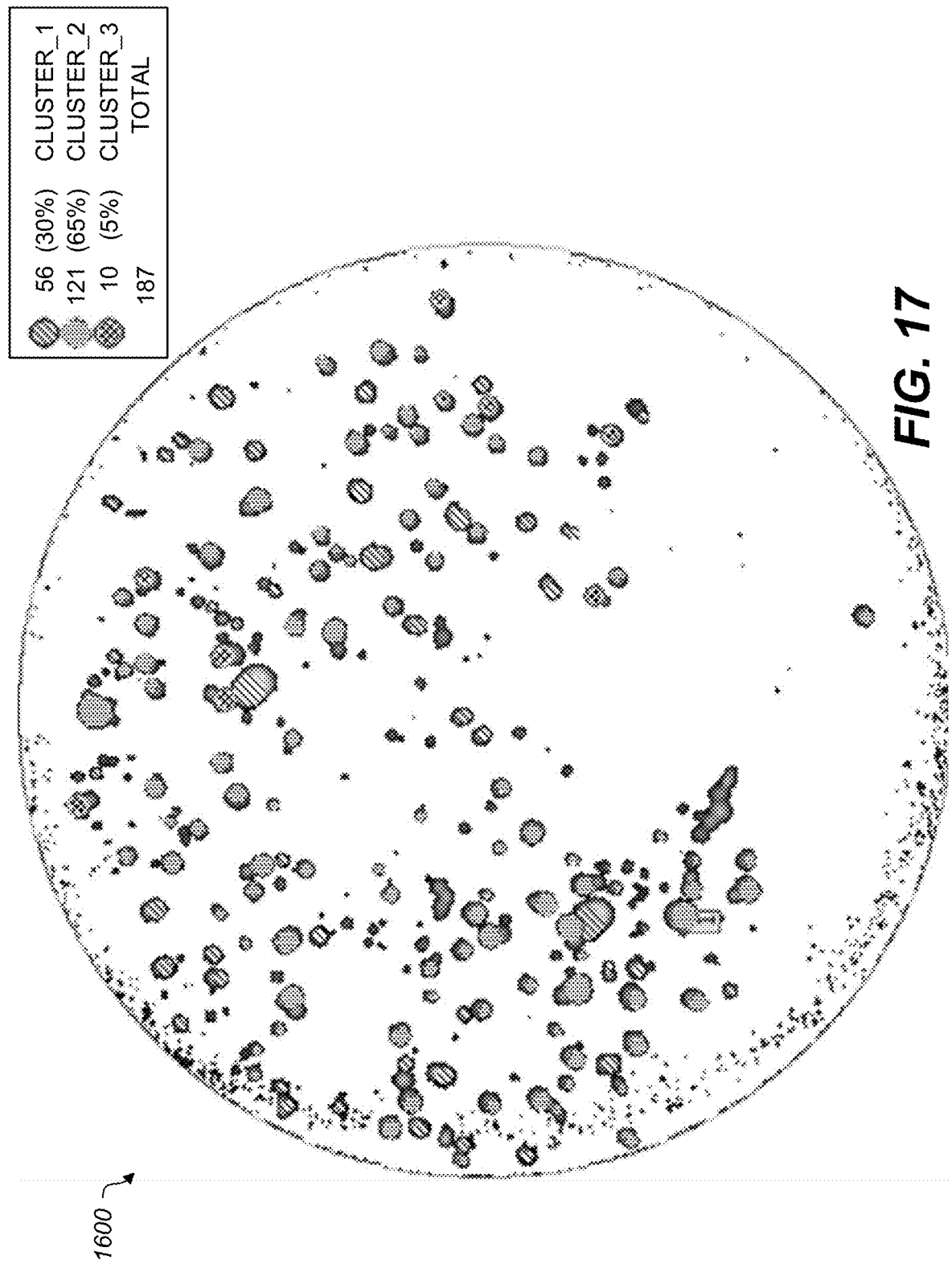
FIG. 17 shows an example cluster map.

FIG. 16 shows an example graphical user interface to select cluster features for determining the clusters that may be illustrated in a colony map 1700 as shown in FIG. 17. The processing to produce colony map 1700 includes calculating Zernike Polynomials and K-Means clustering.

FIG. 17 shows a different example colony map 1700 based on a captured image of a circular plate. Three different types of clusters were identified on the plate based on similarity of characteristics. In this colony map, three different classes identified: cluster 1, cluster 2, and cluster 3. There are a total of 187 different colonies identified. Clusters can be visually identified in a graphical representation of a plate using, e.g., a different color, shape, or hatching pattern for each cluster number, or a respective number, letter, or symbol for each cluster.

The Zernike polynomials are a sequence of polynomials that are orthogonal on the unit disk. The functions are a basis defined over the circular support area, typically the pupil planes in classical optical imaging at visible and infrared wavelengths through systems of lenses and mirrors of finite diameter. Their advantages are the simple analytical properties inherited from the simplicity of the radial functions and the factorization in radial and azimuthal functions; this leads, for example, to closed-form expressions of the two-dimensional Fourier transform in terms of Bessel functions. Their disadvantage, in particular if high n are involved, is the unequal distribution of nodal lines over the unit disk, which introduces ringing effects near the perimeter $\rho \approx 1$, which often leads attempts to define other orthogonal functions over the circular disk. Zernike polynomials are used as basis functions of image moments. Since Zernike polynomials are orthogonal to each other, Zernike moments can represent properties of an image with no redundancy or overlap of information between the moments. Although Zernike moments are significantly dependent on the scaling and the translation of the object in a region of interest (ROI), their magnitudes are independent of the rotation angle of the object. Thus, they can be utilized to extract features from images of colonies that describe the shape characteristics of the colonies. These extract features can be a basis for separating the colonies in a different categories.

Table 3 shows example characteristics of some identified clusters from FIG. 17.

TABLE 3

| No. | Class | Prob | X | Y | Diameter | Roundness | Center X | Center Y |
|---|---|---|---|---|---|---|---|---|
| 1 | Cluster_1 | 0.0 | −15.79 | −17.60 | 0.48 | 0.81 | 255 | 255 |
| 2 | Cluster_2 | 0.0 | −13.61 | −19.95 | 1.71 | 0.71 | 255 | 255 |
| 3 | Cluster_2 | 0.0 | −11.49 | −19.93 | 1.16 | 0.82 | 255 | 255 |
| 4 | Cluster_2 | 0.0 | −13.61 | −15.64 | 1.29 | 0.57 | 255 | 255 |
| 5 | Cluster_2 | 0.0 | −11.50 | −15.87 | 0.86 | 1.01 | 255 | 255 |
| 6 | Cluster_1 | 0.0 | −7.50 | −14.98 | 0.38 | 0.80 | 255 | 255 |
| 7 | Cluster_2 | 0.0 | −9.68 | −13.32 | 0.55 | 1.07 | 255 | 255 |
| 8 | Cluster_2 | 0.0 | −15.63 | −14.98 | 2.01 | 0.67 | 255 | 255 |
| 9 | Cluster_2 | 0.0 | −19.06 | −17.38 | 0.36 | 1.27 | 255 | 255 |
| 10 | Cluster_1 | 0.0 | −21.21 | −18.52 | 0.67 | 1.10 | 255 | 255 |
| 11 | Cluster_2 | 0.0 | −21.98 | −16.00 | 1.25 | 0.95 | 255 | 255 |
| 12 | Cluster_1 | 0.0 | −19.75 | −11.53 | 1.07 | 0.83 | 255 | 255 |

TABLE 3-continued

| No. | Class | Prob | X | Y | Diameter | Roundness | Center X | Center Y |
|---|---|---|---|---|---|---|---|---|
| 13 | Cluster_2 | 0.0 | −16.56 | −12.06 | 0.38 | 0.80 | 255 | 255 |
| 14 | Cluster_2 | 0.0 | −13.52 | −10.04 | 0.77 | 0.82 | 255 | 255 |

Figure 18:
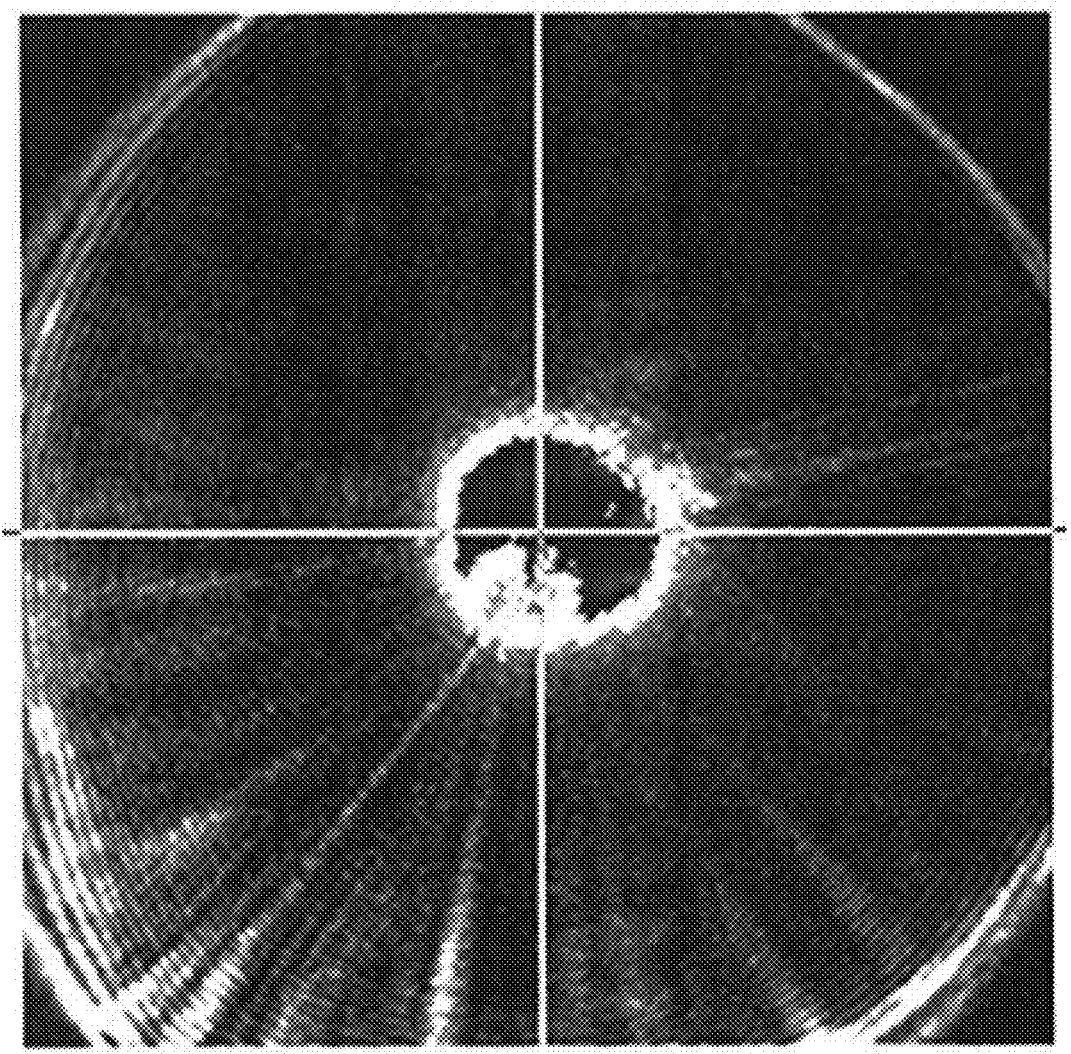
FIG. 18 shows a graphical representation of an example scatter image.

FIG. 18 shows an example scatter image of a single one of the identified clusters from FIG. 16. Analysis of this image through machine vision techniques, calculation of Zernike moments, and the like provides data which goes into Table 3 and which may be used for classification. Using a machine learning technique, which may be a support vector machine (SVM) classifier, decision tree, maximum likelihood classifier, neural networks, or the like, appropriate decision criteria may be developed with respect to the observed features. These features may be embodied in a classification algorithm. The learning process may be either supervised or unsupervised.

Once the features have been obtained, the classification algorithm may separately be used to identify colonies having similar features. Features may be extracted from the images of the scatter images or of the light images, as previously described, and analyzed by the classification algorithm to determine if two colonies are identifiable as likely being a same organism.

Figure 19:
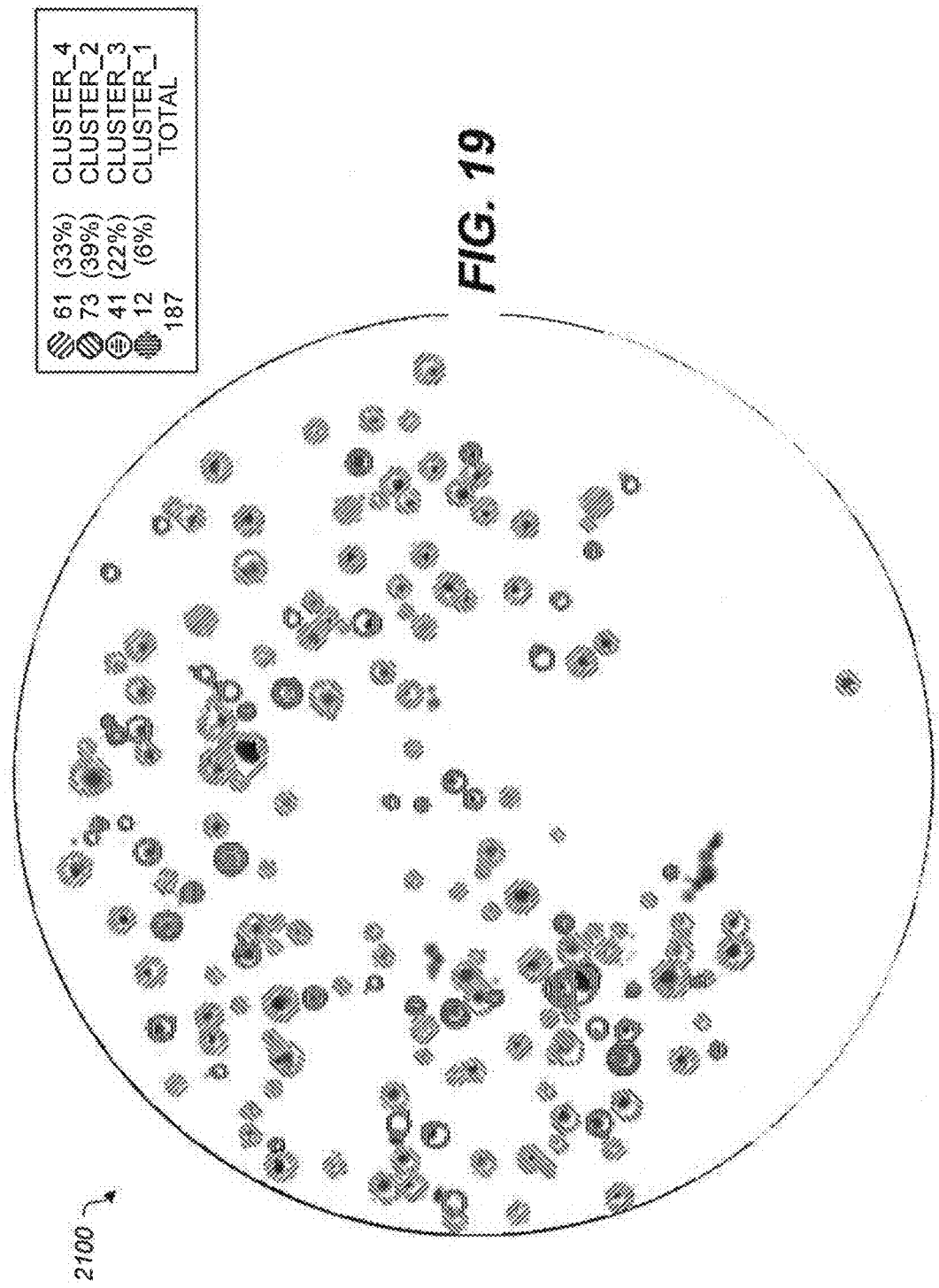
FIG. 19 shows the example cluster map of FIG. 21

FIG. 19 shows another example of a colony map 1900 of a circular plate overlaid with hatched rings indicating four different clusters of colonies. Here, 187 different colonies are clustered into four groups.

Figure 20:
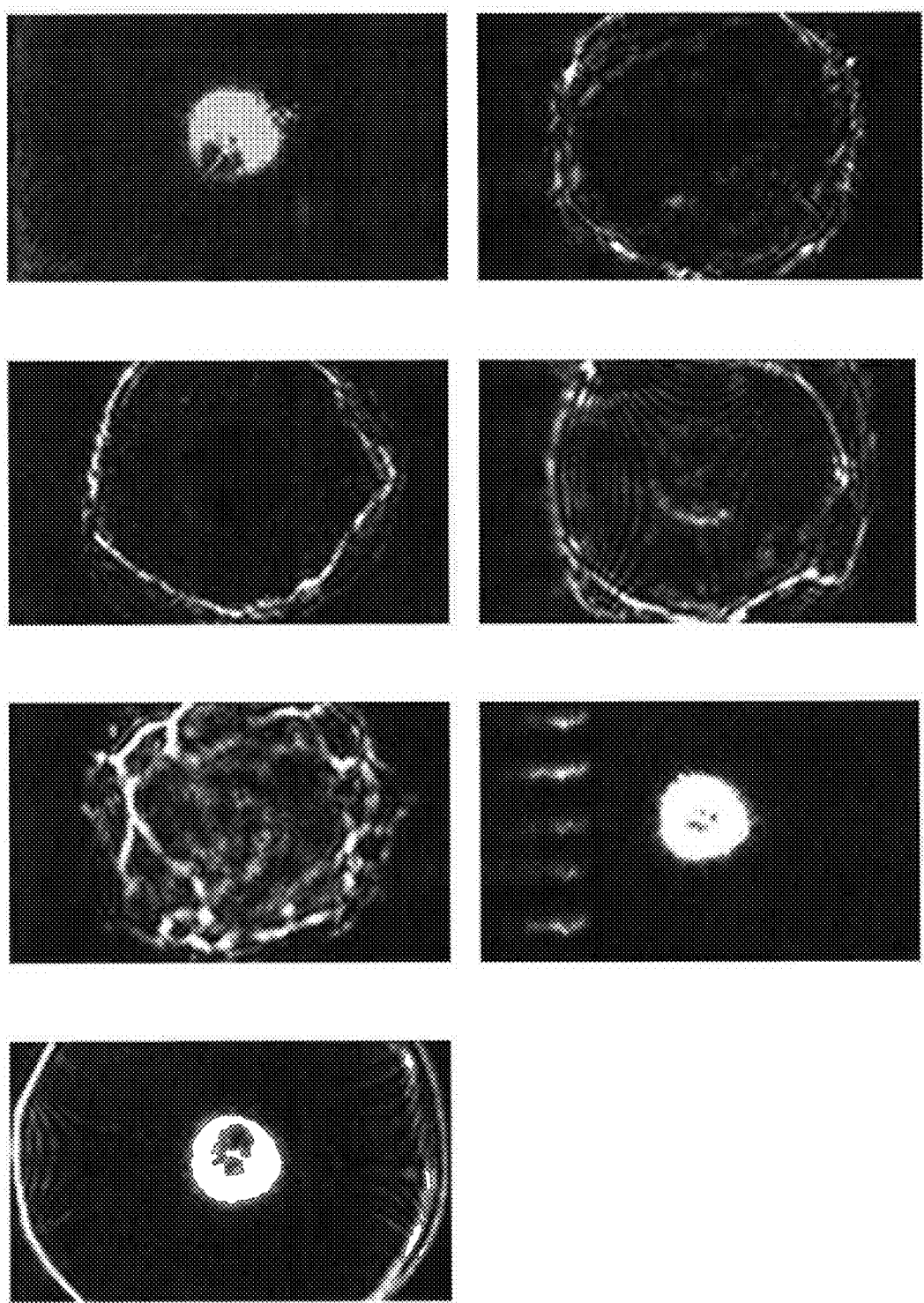
FIG. 20 shows graphical representations of example scatter images.

FIG. 20 shows an example of the diversity of scatter images of representative colonies from various identified clusters.

Figure 21:
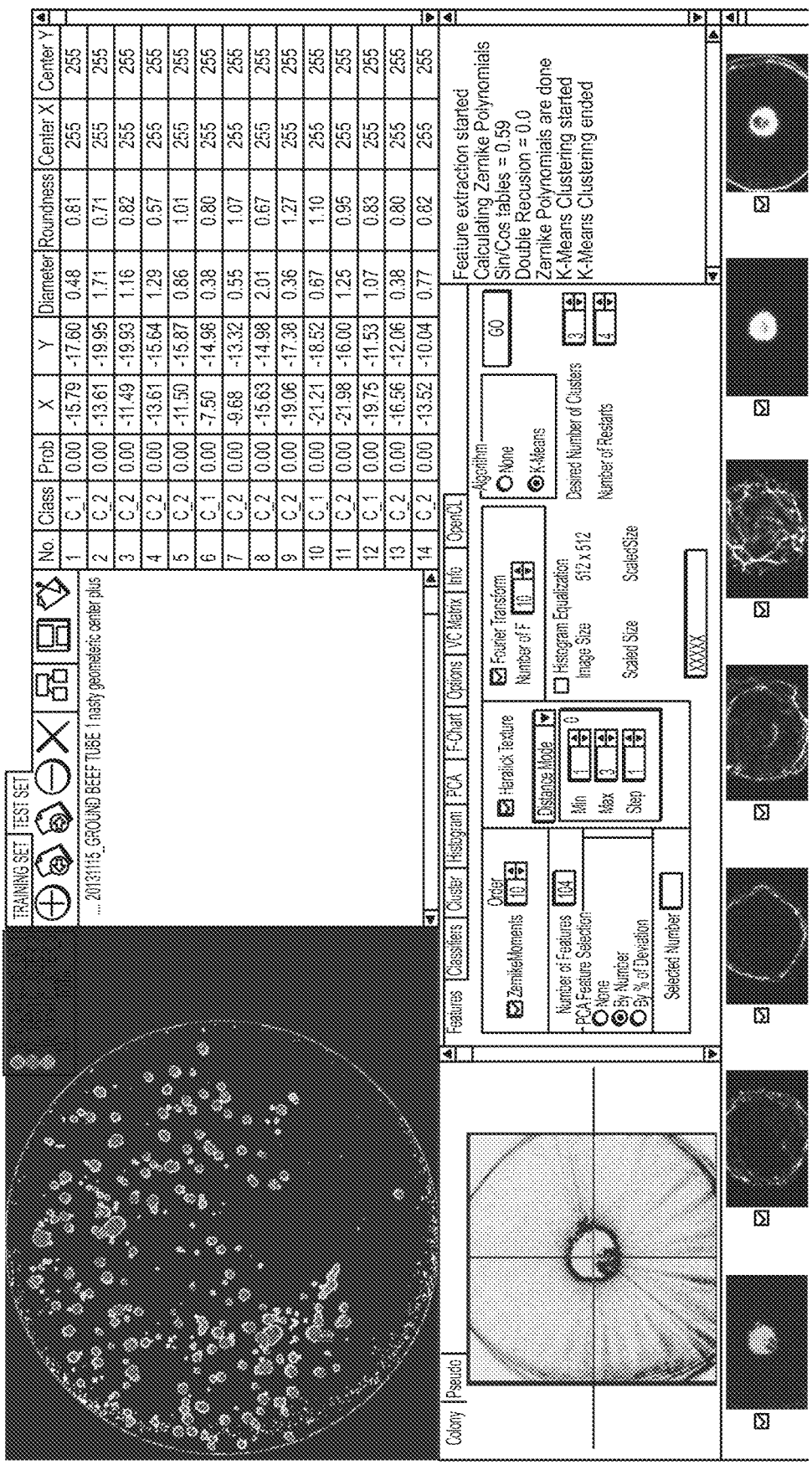
FIG. 21 shows a graphical representation of an example user interface.

FIG. 21 shows an example graphical user interface (e.g., presented to user 2238 by user interface system 2230) for providing clustering parameters and viewing clustering results. This example graphical user interface includes the graphical user interface shown in FIG. 16, the colony map showing FIG. 16, the example scatter image shown FIG. 18, and the representative scatter images shown in FIG. 20.

Table 4 shows the clustering results of 824 scatter images. The 824 scatter images are grouped into 10 distinct clusters.

TABLE 4

| Number | % | Cluster # |
|---|---|---|
| 159 | 19 | 9 |
| 148 | 18 | 10 |
| 152 | 18 | 1 |
| 80 | 10 | 5 |
| 69 | 8 | 8 |
| 147 | 18 | 6 |
| 43 | 5 | 7 |
| 1 | 0 | 2 |
| 19 | 2 | 3 |
| 6 | 1 | 4 |
| 824 total | | |

In view of the foregoing, various aspects provide improved management of culture plates and measurement of colonies. A technical effect is to identify the number of types of colonies. A further technical effect is to present a visual representation of the state of the imaging system, e.g., the locations of colonies on the plate, on an electronic display. Various aspects permit determining how many different sets of similar colonies are on a plate, i.e., the diversity of the plate. Various aspects permit more rapidly and efficiently analyzing data in tests, e.g., to locate organisms that become resistant to antibiotics over time. Various aspects reduce the time and memory required to process plate data by rapidly selecting only organisms of interest on a plate, e.g., based on morphological or other phenotype characteristics, reducing the need for genetic analysis.

Steps of various methods described herein can be performed in any order except when otherwise specified, or when data from an earlier step is used in a later step. Exemplary method(s) described herein are not limited to being carried out by components particularly identified in discussions of those methods.

Example Data-Processing System and Related Components

Figure 22:
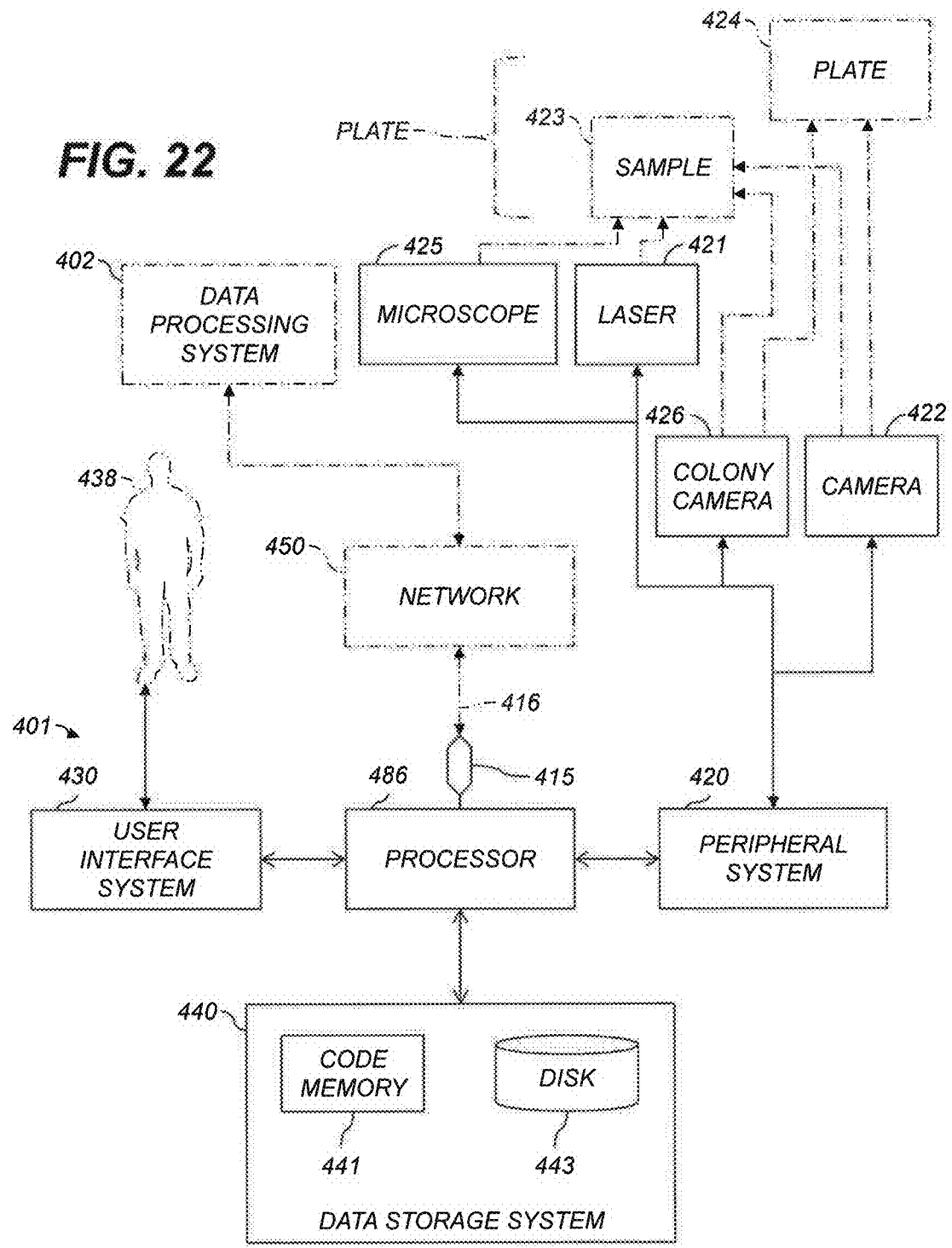
FIG. 22 is a high-level diagram showing the components of a data-processing system.

FIG. 22 is a high-level diagram showing the components of an exemplary data-processing system 2201 for analyzing data and performing other analyses described herein, and related components. The system 2201 includes a processor 2286, a peripheral system 2220, a user interface system 2230, and a data storage system 2240. The peripheral system 2220, the user interface system 2230, and the data storage system 440 are communicatively connected to the processor 2286. Processor 2286 can be communicatively connected to network 2250 (shown in phantom), e.g., the Internet or a leased line, as discussed below. Measurement systems discussed in this disclosure can each include one or more of systems 2221, 2222, 2225, 2226, and can each connect to one or more network(s) 2250.

Processor 2286 can be and/or include one or more single-core processors, multi-core processors, CPUs, GPUs, GPGPUs, and/or hardware logic components configured, e.g., via specialized programming from modules and/or APIs, to perform functions described herein. For example, and without limitation, illustrative types of hardware logic components that can be used in and/or as processor 2286 include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), Digital Signal Processors (DSPs), and other types of customizable processors. For example, a processor 2286 can represent a hybrid device, such as a device from ALTERA and/or XILINX that includes a CPU core embedded in an FPGA fabric. These and/or other hardware logic components can operate independently and/or, in some instances, can be driven by a CPU. In some examples, at least some of system 2201, can include a plurality of processors 2286 of multiple types. For example, the processor 2286 in computing device 2201 can be a combination of one or more GPGPUs and one or more FPGAs. Different processors 2286 can have different execution models, e.g., as is the case for graphics processing units (GPUs) and central processing unit (CPUs). In some examples at least one processor 2286, e.g., a CPU, graphics processing unit (GPU), and/or hardware logic device, can be incorporated in system 2201, while in some examples at least one processors 2286, e.g., one or more of a CPU, GPU, and/or hardware logic device, can be external to system 2201.

In some examples of hardware configurations, e.g., ASICs, modules configured to perform functions or operations described herein can be embodied in or can represent logic blocks designed into the hardware. Such modules, in some examples, are considered to be stored within the hardware configuration. In some examples of firmware configurations, e.g., FPGAs, modules described herein can be embodied in or can represent logic blocks specified, e.g., by a configuration bitstream stored in a nonvolatile memory such as a Flash memory or read-only memory (ROM). Such modules, in some examples, are considered to be stored within the nonvolatile memory. The nonvolatile memory can be included within the FPGA or other device implementing the logic blocks, or can be separate therefrom (e.g., a configuration memory such as an ALTERA EPCS16).

Processor 2286 can implement processes of various aspects described herein, such as image-capturing and image-processing processes described herein. Processor 2286 and related components can, e.g., carry out processes for any combination of capturing whole-plate images, presenting plate images via user interface system 2230, detecting colony locations, aiming the laser according to the detected locations of colonies, capturing scatter images using the laser, capturing light images using the colony camera, presenting captured light and scatter images via user interface system 2230, determining features of colonies based on light images (whole-plate or magnified per-colony) or scatter images, clustering the determined features, and presenting a digital colony map image via user interface system 2230, e.g., as shown in FIG. 20.

Processor 2286 can be or include one or more device(s) for automatically operating on data, e.g., a central processing unit (CPU), microcontroller (MCU), desktop computer, laptop computer, mainframe computer, personal digital assistant, digital camera, cellular phone, smartphone, or any other device for processing data, managing data, or handling data, whether implemented with electrical, magnetic, optical, biological components, or otherwise.

The phrase "communicatively connected" includes any type of connection, wired or wireless, for communicating data between devices or processors. These devices or processors can be located in physical proximity or not. For example, subsystems such as peripheral system 2220, user interface system 2230, and data storage system 2240 are shown separately from the data processing system 2202 but can be stored completely or partially within the data processing system 2202.

The peripheral system 2220 can include or be communicatively connected with one or more devices configured or otherwise adapted to provide digital content records to the processor 2286 or to take action in response to processor 2286. For example, the peripheral system 2220 can include digital still cameras, digital video cameras, cellular phones, or other data processors. The processor 2286, upon receipt of digital content records from a device in the peripheral system 2220, can store such digital content records in the data storage system 2240.

In some examples, peripheral system 2220 includes, operates, or is communicatively connected with laser 2221 that measures diffraction patterns from one or more samples 2223, e.g., colonies, on a culture plate 2224 as described above. In some examples, peripheral system 2220 includes, operates, or is communicatively connected with a camera 2222 that captures light images of culture plates 2224 or fiducials, markings, or colonies thereon as described herein. A colony camera 2226 may capture light images of individual colonies magnified by a microscope 2225. The microscope 2225 may have adjustable magnification so that the camera 2222 is able to capture different images of a same colony representing the colony at different levels of magnification. The microscope 2225 may operate in conjunction with a filtering unit (not shown) that provides various optical or electronic filtering.

The user interface system 2230 can convey information in either direction, or in both directions, between a user 2238 and the processor 2286 or other components of system 2201. The user interface system 2230 can include a mouse, a keyboard, another computer (connected, e.g., via a network or a null-modem cable), or any device or combination of devices from which data is input to the processor 2286. The user interface system 2230 also can include a display device, a processor-accessible memory, or any device or combination of devices to which data is output by the processor 2286. The user interface system 2230 and the data storage system 2240 can share a processor-accessible memory. In an implementation, the graphical user interfaces shown FIGS. 17 and 21 may be presented to the user 2238 by the user interface system 2230.

In various aspects, processor 2286 includes or is connected to communication interface 2215 that is coupled via network link 2216 (shown in phantom) to network 2250. For example, communication interface 2215 can include an integrated services digital network (ISDN) terminal adapter or a modem to communicate data via a telephone line; a network interface to communicate data via a local-area network (LAN), e.g., an Ethernet LAN, or wide-area network (WAN); or a radio to communicate data via a wireless link, e.g., WIFI or GSM. Communication interface 2215 sends and receives electrical, electromagnetic, or optical signals that carry digital or analog data streams representing various types of information across network link 2216 to network 2250. Network link 2216 can be connected to network 2250 via a switch, gateway, hub, router, or other networking device.

In various aspects, system 2201 can communicate, e.g., via network 2250, with a data processing system 2202, which can include the same types of components as system 2201 but is not required to be identical thereto. Systems 2201, 2202 are communicatively connected via the network 2250. Each system 2201, 2202 executes computer program instructions to perform processes described herein. In some examples, system 2201 can operate the laser 2221 and system 2202 can operate the camera 2222.

Processor 2286 can send messages and receive data, including program code, through network 2250, network link 2216, and communication interface 2215. For example, a server can store requested code for an application program (e.g., a JAVA applet) on a tangible non-volatile computer-readable storage medium to which it is connected. The server can retrieve the code from the medium and transmit it through network 2250 to communication interface 2215. The received code can be executed by processor 2286 as it is received, or stored in data storage system 2240 for later execution.

Data storage system 2240 can include or be communicatively connected with one or more processor-accessible memories configured or otherwise adapted to store information. The memories can be, e.g., within a chassis or as parts of a distributed system. The phrase "processor-accessible memory" is intended to include any data storage device to or from which processor 2286 can transfer data (using appropriate components of peripheral system 2220), whether volatile or nonvolatile; removable or fixed; electronic, magnetic, optical, chemical, mechanical, or otherwise. Exemplary processor-accessible memories include but are not limited to: registers, floppy disks, hard disks, tapes, bar codes, Compact Discs, DVDs, read-only memories (ROM), erasable programmable read-only memories (EPROM, EEPROM, or Flash), and random-access memories (RAMs). One of the processor-accessible memories in the data storage system 2240 can be a tangible non-transitory computer-readable storage medium, i.e., a non-transitory device or article of manufacture that participates in storing instructions that can be provided to processor 2286 for execution.

In an example, data storage system 2240 includes code memory 2241, e.g., a RAM, and disk 2243, e.g., a tangible computer-readable rotational storage device or medium such as a hard drive. Computer program instructions are read into code memory 2241 from disk 2243. Processor 2286 then executes one or more sequences of the computer program instructions loaded into code memory 2241, as a result performing process steps described herein. In this way, processor 2286 carries out a computer implemented process. For example, steps of methods described herein, blocks of the flowchart illustrations or block diagrams herein, and combinations of those, can be implemented by computer program instructions. Code memory 2241 can also store data, or can store only code.

Various aspects described herein can be embodied as systems or methods. Accordingly, various aspects herein can take the form of an entirely hardware aspect, an entirely software aspect (including firmware, resident software, micro-code, etc.), or an aspect combining software and hardware aspects These aspects can all generally be referred to herein as a "service," "circuit," "circuitry," "module," or "system."

Furthermore, various aspects herein can be embodied as computer program products including computer readable program code ("program code") stored on a computer readable medium, e.g., a tangible non-transitory computer storage medium or a communication medium. A computer storage medium can include tangible storage units such as volatile memory, nonvolatile memory, or other persistent or auxiliary computer storage media, removable and non-removable computer storage media implemented in any method or technology for storage of information such as computer-readable instructions, data structures, program modules, or other data. A computer storage medium can be manufactured as is conventional for such articles, e.g., by pressing a CD-ROM or electronically writing data into a Flash memory. In contrast to computer storage media, communication media can embody computer-readable instructions, data structures, program modules, or other data in a modulated data signal, such as a carrier wave or other transmission mechanism. As defined herein, computer storage media do not include communication media. That is, computer storage media do not include communications media consisting solely of a modulated data signal, a carrier wave, or a propagated signal, per se.

The program code includes computer program instructions that can be loaded into processor 2286 (and possibly also other processors), and that, when loaded into processor 2286, cause functions, acts, or operational steps of various aspects herein to be performed by processor 2286 (or other processor). Computer program code for carrying out operations for various aspects described herein can be written in any combination of one or more programming language(s), and can be loaded from disk 2243 into code memory 2241 for execution. The program code can execute, e.g., entirely on processor 2286, partly on processor 2286 and partly on a remote computer connected to network 2250, or entirely on the remote computer.

Example Clauses

Throughout these example clauses, parenthetical remarks are examples and are not limiting. Examples given in the parenthetical remarks of specific example clauses can also apply to the same terms appearing elsewhere in these example clauses.

Clause A. A system for the characterization of a colony of microorganisms, the system comprising:
  a coherent light source configured to provide coherent light;
  a holder configured to operationally arrange a substrate so that the colony of microorganisms on a surface of the substrate is positioned to receive the coherent light and generate scattered light from the colony of microorganisms receiving the coherent light;
  a first image capture device configured to receive the scattered light and generate a scatter image associated with the scattered light;
  a magnifying lens; and
  a second image capture device configured to capture a light image of the colony of microorganisms magnified by the magnifying lens.

Clause B. The system according to clause A, wherein the holder is further configured to operationally arrange the substrate so that the magnifying lens occupies an optical path between the colony of microorganisms on the substrate and the second image capture device.

Clause C. The system according to either clause A or B, wherein the first image capture device is arranged on a first side of the substrate and the coherent light source, the magnifying lens, and the second image capture device are arranged on a second side of the substrate.

Clause D. The system according to any one of clauses A-C, further comprising a third image capture device configured to capture a plate image of substantially the entire surface of the substrate.

Clause E. The system according to clause D, wherein the second image capture device is configured to capture the light image at a first level of magnification and the third image capture device is configured to capture the plate image at a second level of magnification less than the first level of magnification.

Clause F. The system according to clause E, wherein the second image capture device is further configured to capture an additional light image at a second level of magnification greater than first level of magnification.

Clause G. The system according to any one of clauses A-F, further comprising a filtering unit configured to modify the light image.

Clause H. A computer-implemented method for identifying a number of microorganism types in a set of multiple colonies of microorganisms, the method comprising:
  receiving a plurality of images, each image associated with a different single colony of microorganisms from the set of multiple colonies of microorganisms;
  determining, using a processor, a first set of image features, the first set of image features including at least one image feature for each image of at least a portion of the plurality of images; and
  determining, using the processor and based at least in part on the first set of image features, a first group of colonies including at least a first colony of the multiple colonies of microorganisms and a second group of colonies including at least a second, different colony of the multiple colonies of microorganisms.

Clause I. The computer-implemented method according to clause H, further comprising imaging at least some colonies of the set of multiple colonies of microorganisms through a magnifying lens using an image capture device to provide respective light images.

Clause J. The computer-implemented method according to either clause H or I, further comprising capturing, using an image capture device, a plurality of scatter patterns created by coherent light passing through respective colonies of the set of multiple colonies of microorganisms.

Clause K. The computer-implemented method according to any one of clauses H-J, wherein each image of the plurality of images is an image of a scatter pattern representing light scattered by a respective colony of microorganisms under coherent illumination, the method further comprising:

receiving a plurality of light images, each light image showing a magnified view of a respective colony of the set of multiple colonies of microorganisms;

determining, using the processor, a second set of image features, the second set of image features including at least one light image feature for the individual ones of at least the portion of the plurality of images; and determining the first group of colonies and the second group of colonies based at least in further part on the second set of image features.

Clause L. The computer-implemented method according to any one of clauses H-K, wherein the determining the first group of colonies and the second group of colonies identities includes clustering the set of image features based on least in part on at least one of a parametric clustering technique or a nonparametric clustering techniques.

Clause M. The computer-implemented method according to clause L, wherein the clustering is based at least in part on the parametric clustering technique and the method further comprises:

performing multiple instances of the parametric clustering technique using a different numbers of clusters for each of the multiple instances to provide respective clustering result sets;

determining, using the processor, a respective level of cluster compactness associated with each of the clustering result sets;

determining, using the processor, a one of the clustering result sets having a level of cluster compactness greater than any of the other clustering result sets to determine a most compact clustering result set; and determining that the number of microorganism types is the number of clusters associated with the most compact clustering result set.

Clause N. The computer-implemented method according to any one of clauses H-M, further comprising:

receiving a plate image of substantially the entire surface of a substrate, the set of multiple colonies of microorganisms being disposed upon the surface of the substrate; and generating a colony map from at least a portion of the plate image, the colony map indicating individual colonies of the first group of colonies with respective first markings and indicating individual colonies of the a second group of colonies with respective second markings.

Clause O. A system comprising:

a coherent light source configured to provide coherent light;

a first image capture device configured to capture a scatter image from a scatter pattern generated by the coherent light impinging on a colony of microorganisms associated with a substrate;

a magnifying lens;

a second image capture device configured to generate a light image depicting the colony of microorganisms; and a positioning system configure to change relative positioning of at least two of the substrate, the coherent light source, and the magnifying lens.

Clause P. The system of clause O, wherein the positioning system is configured to change the relative positioning between a first position in which the coherent light passes through the colony of microorganism and a second position in which the magnifying lens occupies an optical path between the colony of microorganisms and the second image capture device.

Clause Q. The system of either clause O or P, wherein the substrate is further associated with multiple colonies of microorganisms and the system further comprises:

a processor;

a memory; and computer program instructions stored in the memory or implemented in hardware to:

determine a first set of image features from the scatter image;

determine a second set of image features from the light image;

group, at least a portion of the multiple colonies of microorganism into a plurality of groups; and associate the colony of microorganisms with a first group of the plurality of groups based at least in part on the first set of image features and the second set of image features.

Clause R. The system of clause Q, wherein the second set of image features includes at least one of form, size, border, surface, opacity, polarization state, or color.

Clause S. The system of either clause Q or R, wherein the computer program instructions are further implemented to present a user interface that includes a colony map graphically depicting:

a position of the colony of microorganisms;

respective positions of a plurality of other colonies of microorganisms of the multiple colonies of microorganisms;

an indication of an association of the colony of microorganisms with the first group; and indications of respective associations between the plurality of groups and individual colonies of the plurality of other colonies of microorganisms.

Clause T. The system of any one of clauses O-S, further comprising:

a processor;

a memory; and computer program instructions stored in the memory or implemented in hardware to:

determine a first set of image features from the scatter image;

determine that the first set of image features is insufficient to determine a group classification associated with the colony of microorganisms;

determine a second set of features from the light image; and determine, based at least in part on the first set of features and the second set of features, the group classification of the colony of microorganisms.

CONCLUSION

Throughout this description, some aspects are described in terms that would ordinarily be implemented as software programs. Those skilled in the art will readily recognize that the equivalent of such software can also be constructed in hardware, firmware, or micro-code. Because data-manipulation algorithms and systems are well known, the present description is directed in particular to algorithms and systems forming part of, or cooperating more directly with, systems and methods described herein. Other aspects of such algorithms and systems, and hardware or software for producing and otherwise processing signals or data involved therewith, not specifically shown or described herein, are selected from such systems, algorithms, components, and elements known in the art. Given the systems and methods as described herein, software not specifically shown, suggested, or described herein that is useful for implementation of any aspect is conventional and within the ordinary skill in such arts.

Individual operations of example processes discussed herein can represent one or more operations that can be implemented in hardware, firmware, software, and/or a combination thereof. In the context of software, for example, the operations represent computer-executable instructions stored on one or more computer-readable media that, when executed by one or more processors, enable the one or more processors to perform the recited operations. Generally, computer-executable instructions include routines, programs, objects, modules, components, data structures, and the like that perform particular functions and/or implement particular abstract data types. The order in which the operations are described is not intended to be construed as a limitation, and any number of the described operations can be executed in any order, combined in any order, subdivided into multiple sub-operations, and/or executed in parallel to implement the described processes. The described processes can be performed by resources associated with one or more computing device(s) 2201 such as one or more internal and/or external CPUs and/or GPUs, and/or one or more pieces of hardware logic such as FPGAs, DSPs, and/or other types described above.

All of the methods and processes described above can be embodied in, and fully automated via, software code modules executed by one or more computers and/or processors. The code modules can be embodied in any type of computer-readable medium. Some and/or all of the methods can be embodied in specialized computer hardware, e.g., ASICs.

Various aspects are inclusive of combinations of the aspects described herein. References to "a particular aspect" (or "embodiment" or "version") and the like refer to features that are present in at least one aspect of the invention. Separate references to "an aspect" (or "embodiment") or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting. The word "or" and the phrase "and/or" are used herein in an inclusive sense unless specifically stated otherwise. Accordingly, conjunctive language such as, but not limited to, at least the phrases "X, Y, or Z," "at least X, Y, or Z," "at least one of X, Y or Z," and/or any of those phrases with "and/or" substituted for "or," unless specifically stated otherwise, is to be understood as signifying that an item, term, etc., can be either X, Y, or Z, or a combination of any elements thereof (e.g., a combination of XY, XZ, YZ, and/or XYZ).

The invention has been described in detail with particular reference to certain preferred aspects thereof, but it will be understood that variations, combinations, and modifications can be effected by a person of ordinary skill in the art within the spirit and scope of the invention.

The invention claimed is:

1. A computer-implemented method for identifying a number of microorganism types in a set of multiple colonies of microorganisms, the method comprising:
    receiving a plurality of images, each image associated with a different single colony of microorganisms from the set of multiple colonies of microorganisms;
    determining, using a processor, a first set of image features, the first set of image features including at least one image feature for each image of at least a portion of the plurality of images;
    determining, using the processor and based at least in part on the first set of image features, a first group of colonies including at least a first colony of the multiple colonies of microorganisms and a second group of colonies including at least a second, different colony of the multiple colonies of microorganisms, wherein the determining the first group of colonies and the second group of colonies identities includes clustering the set of image features based on least in part on at least one of a parametric clustering technique or a nonparametric clustering techniques, and wherein the clustering is based at least in part on the parametric clustering technique;
    performing multiple instances of the parametric clustering technique using a different numbers of clusters for each of the multiple instances to provide respective clustering result sets;
    determining, using the processor, a respective level of cluster compactness associated with each of the clustering result sets;
    determining, using the processor, a one of the clustering result sets having a level of cluster compactness greater than any of the other clustering result sets to determine a most compact clustering result set; and
    determining that the number of microorganism types is the number of clusters associated with the most compact clustering result set.

2. The computer-implemented method according to claim 1, further comprising imaging at least some colonies of the set of multiple colonies of microorganisms through a magnifying lens using an image capture device to provide respective light images.

3. The computer-implemented method according to claim 1, further comprising capturing, using an image capture device, a plurality of scatter patterns created by coherent light passing through respective colonies of the set of multiple colonies of microorganisms.

4. The computer-implemented method according to claim 1, wherein each image of the plurality of images is an image of a scatter pattern representing light scattered by a respective colony of microorganisms under coherent illumination, the method further comprising:
    receiving a plurality of light images, each light image showing a magnified view of a respective colony of the set of multiple colonies of microorganisms;
    determining, using the processor, a second set of image features, the second set of image features including at least one light image feature for the individual ones of at least the portion of the plurality of images; and
    determining the first group of colonies and the second group of colonies based at least in further part on the second set of image features.

5. The computer-implemented method according to claim 1, further comprising:
   receiving a plate image of substantially the entire surface of a substrate, the set of multiple colonies of microorganisms being disposed upon the surface of the substrate; and
   generating a colony map from at least a portion of the plate image, the colony map indicating individual colonies of the first group of colonies with respective first markings and indicating individual colonies of the second group of colonies with respective second markings.

* * * * *